US010266861B2

(12) United States Patent
Nagy et al.

(10) Patent No.: US 10,266,861 B2
(45) Date of Patent: *Apr. 23, 2019

(54) PRODUCTION AND COMPOSITION OF FRUCTOSE SYRUP

(71) Applicant: E I DU PONT DE NEMOURS AND COMPANY, Wilmington, DE (US)

(72) Inventors: Kevin D Nagy, Wilmington, DE (US); Susan Marie Hennessey, Avondale, PA (US); Mark S Payne, Wilmington, DE (US); Charles R Powley, Wilmington, DE (US); Bogdan Szostek, Wilmington, DE (US); Hannu Koivikko, Kantvik (FI); Juho Jarvinen, Kantvik (FI); Daniel Eicholtz, Philadelphia, PA (US); Jyrki Kuusisto, Vantaa (FI); Tapio Timo Viljava, Kantvik (FI); Stephen Thomas Breske, Wilmington, DE (US)

(73) Assignees: E. I. DU PONT DE NEMOURS AND COMPANY, Wilmington, DE (US); DUPONT NUTRITION BIOSCIENCES APS, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/967,659

(22) Filed: Dec. 14, 2015

(65) Prior Publication Data
US 2017/0166938 A1 Jun. 15, 2017

(51) Int. Cl.
| C12P 19/02 | (2006.01) |
| C07H 1/06 | (2006.01) |
| C07H 3/02 | (2006.01) |
| C12P 19/14 | (2006.01) |
| A23L 1/09 | (2006.01) |
| C12P 19/18 | (2006.01) |
| C13K 11/00 | (2006.01) |
| A23L 29/30 | (2016.01) |

(52) U.S. Cl.
CPC ............. *C12P 19/02* (2013.01); *A23L 1/09* (2013.01); *A23L 29/30* (2016.08); *C07H 1/06* (2013.01); *C07H 3/02* (2013.01); *C12P 19/14* (2013.01); *C12P 19/18* (2013.01); *C13K 11/00* (2013.01); *A23V 2002/00* (2013.01)

(58) Field of Classification Search
CPC .. A23L 1/09; A23L 29/30; C07H 1/06; C07H 3/02; C12P 19/14; C12P 19/18; C12P 19/02; C13K 11/00; A23V 2002/00
See application file for complete search history.

(56) References Cited

U.S. PATENT DOCUMENTS

| 4,335,207 | A | 6/1982 | Heady |
| 4,634,472 | A | 1/1987 | Niekamp et al. |
| 4,693,974 | A | 9/1987 | Schwengers et al. |
| 4,713,333 | A | 12/1987 | Chiang et al. |
| 4,797,360 | A | 1/1989 | Doelle |
| 4,927,757 | A | 5/1990 | Hatcher et al. |
| 5,541,097 | A | 7/1996 | Lantero et al. |
| 5,952,205 | A | 9/1999 | Catani et al. |
| 6,242,225 | B1 | 6/2001 | Catani et al. |
| 6,265,635 | B1 | 7/2001 | Kossmann et al. |
| 6,660,502 | B2 | 12/2003 | Catani et al. |
| 7,000,000 | B1 | 2/2006 | O'Brien |
| 7,229,801 | B2 | 6/2007 | Fujii et al. |
| 8,828,689 | B2 | 9/2014 | Caimi et al. |
| 8,871,474 | B2 | 10/2014 | Payne et al. |
| 8,962,282 | B2 | 2/2015 | Caimi et al. |
| 2009/0123603 | A1 | 5/2009 | Carlson et al. |
| 2013/0244288 | A1 | 9/2013 | O'Brien et al. |
| 2014/0336338 | A1 | 11/2014 | Mattila et al. |
| 2015/0004649 | A1* | 1/2015 | Payne ............... C08B 37/0009 435/97 |
| 2015/0216219 | A1 | 8/2015 | Prakash et al. |
| 2015/0240278 | A1 | 8/2015 | Nagy et al. |
| 2015/0240279 | A1 | 8/2015 | Nagy et al. |
| 2015/0257422 | A1 | 9/2015 | Adamski-Werner et al. |
| 2015/0282513 | A1 | 10/2015 | Cook et al. |
| 2015/0313265 | A1 | 11/2015 | Jia et al. |

FOREIGN PATENT DOCUMENTS

| EP | 0315496 E1 | 9/1993 |
| EP | 2292803 A1 | 9/2011 |
| WO | 2015123063 A1 | 8/2015 |

OTHER PUBLICATIONS

Abo et al., Peptide Sequences for Sucrose Splitting and Glucan Binding Within Streptococcus Sobrinus Glucosyltransferase (Water-Insoluble Glucan Synthetase), Journal of Bacteriology, vol. 173, No. 3 (1991), pp. 989-996.

Adrio et al., Microbial Enzymes: Tools for Biotechnological Processes, Biomolecules, vol. 4 (2014), pp. 117-139.

Cantarel et al., The Carbohydrate-Active Enzymes Database (CAZY): An Expert Resource for Glycogenomics, Nucleic Acids Research vol. 37 (2009), Database Issue D233-D238.

Giffard et al., Molecular Characterization of a Cluster of At Least Two Glucosyltransferase Genes in Streptococcus Salivarious ATCC 25975, Journal of General Microbiology, vol. 137 (1991), pp. 2577-2593.

(Continued)

Primary Examiner — Lezah Roberts

(57) ABSTRACT

Disclosed herein are aqueous compositions comprising fructose and methods of production thereof. A method for producing an aqueous composition comprising fructose can comprise, for example, conducting an enzymatic reaction by contacting water, sucrose, and a glucosyltransferase enzyme that synthesizes poly alpha-1,3-glucan having at least 30% alpha-1,3-linkages. A soluble fraction produced by such a reaction comprises at least about 55% fructose on a dry weight basis, and can be separated from insoluble poly alpha-1,3-glucan product(s), thereby providing an aqueous composition comprising fructose.

7 Claims, 2 Drawing Sheets

Specification includes a Sequence Listing.

(56) References Cited

OTHER PUBLICATIONS

Kingston et al., Role of the C-Terminal YG Repeats of the Primer-Dependent Streptococcal Glucosyltransferase, GTFJ, In Binding to Dextran and Mutan, Microbiology, vol. 148, pp. 549-558.

Komatsu et al., Kinetics of Dextran-Independent α-(1—>3)-Glucan Synthesis by Streptococcus Sobrinus Glucosyltransferase I, FEBS Journal, vol. 278 (2011), pp. 531-540.

Mason et al., A Gas Chromatographic Method for the Determination of Sugars in Foods, J. Agr. Food Chem., vol. 19, No. 3 (1971), pp. 551-554.

Monchois et al., Glucansucrases: Mechanism of Action and Structure-Function Relationships, FEMS Microbiology Reviews, vol. 23 (1999), pp. 131-151.

Monchois et al., Isolation of an Active Catalytic Core of Streptococcus Downei MFE28 GTF-1 Glucosyltransferase, Journal of Bacteriology, vol. 181, No. 7 (1999), pp. 2290-2292.

Moulik et al., Production of Fructose Sugar From Aqueous Solutions: Nanofiltration Performance and Hydrodynamic Analysis, Journal of Cleaner Production, vol. 92 (2015), pp. 44-53.

Simpson et al., Four Glucosyltransferases, GTFJ, GTFK, GTFL and GTFM, From Streptococcus ATCC 25975, Microbiology, vol. 141 (1995), pp. 1451-1460.

Van Hijum et al., Structure-Function Relationships of Glucansucrase and Fructansucrase Enzymes From Lactic Acid Bacteria, Microbiology and Molecular Biology Reviews, vol. 70, No. 1 (2006), pp. 157-176.

Annex to Form PCT/ISA206, Communication Relating to the Results of the Partial International Search, Corresponding PCT Application No. PCT/US2016/066517, dated Mar. 29, 2017.

Van Hijun et al., Structure-Function Relationships of Glucansucrase and Fructansucrase Enzymes from Lactic Acid Bacteria, Microbiology and Molecular Biology Reviews, vol. 70, No. 1 (2006), pp. 157-176.

\* cited by examiner

```
                        SEQUENCE LISTING

<160> NUMBER OF SEQ ID NOS: 6

<210> SEQ ID NO 1
<211> LENGTH: 1341
<212> TYPE: PRT
<213> ORGANISM: Streptococcus salivarius

<400> SEQUENCE: 1

Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
            35                  40                  45

Thr Asn Ile Val Asp Gly Phe Ser Ile Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
            115                 120                 125

Leu Asp Ala Lys Tyr Ser Ser Thr Asp Lys Gln Glu Thr Leu Lys Val
        130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly
            180                 185                 190
```

-continued

Glu Asp His Leu Gln Gly Gly Ala Leu Leu Tyr Val Asn Asp Ser Arg
            195                 200                 205

Thr Pro Trp Ala Asn Ser Asp Tyr Arg Arg Leu Asn Arg Thr Ala Thr
210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
            290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
            515                 520                 525

Asn Leu Met Lys Ser Arg Ile Lys Tyr Val Ser Gly Gly Gln Ala Gln
            530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Asn Leu Asp
            595                 600                 605

Gln Ser Ala Lys Leu Asn Val Glu Met Gly Lys Ile His Ala Asn Gln

```
                610             615             620
Lys Tyr Arg Ala Leu Ile Val Gly Thr Ala Asp Gly Ile Lys Asn Phe
625             630             635             640

Thr Ser Asp Ala Asp Ala Ile Ala Ala Gly Tyr Val Lys Glu Thr Asp
            645             650             655

Ser Asn Gly Val Leu Thr Phe Gly Ala Asn Asp Ile Lys Gly Tyr Glu
            660             665             670

Thr Phe Asp Met Ser Gly Phe Val Ala Val Trp Val Pro Val Gly Ala
            675             680             685

Ser Asp Asn Gln Asp Ile Arg Val Ala Pro Ser Thr Glu Ala Lys Lys
            690             695             700

Glu Gly Glu Leu Thr Leu Lys Ala Thr Glu Ala Tyr Asp Ser Gln Leu
705             710             715             720

Ile Tyr Glu Gly Phe Ser Asn Phe Gln Thr Ile Pro Asp Gly Ser Asp
            725             730             735

Pro Ser Val Tyr Thr Asn Arg Lys Ile Ala Glu Asn Val Asp Leu Phe
            740             745             750

Lys Ser Trp Gly Val Thr Ser Phe Glu Met Ala Pro Gln Phe Val Ser
            755             760             765

Ala Asp Asp Gly Thr Phe Leu Asp Ser Val Ile Gln Asn Gly Tyr Ala
            770             775             780

Phe Ala Asp Arg Tyr Asp Leu Ala Met Ser Lys Asn Asn Lys Tyr Gly
785             790             795             800

Ser Lys Glu Asp Leu Arg Asp Ala Leu Lys Ala Leu His Lys Ala Gly
            805             810             815

Ile Gln Ala Ile Ala Asp Trp Val Pro Asp Gln Ile Tyr Gln Leu Pro
            820             825             830

Gly Lys Glu Val Val Thr Ala Thr Arg Thr Asp Gly Ala Gly Arg Lys
            835             840             845

Ile Ala Asp Ala Ile Ile Asp His Ser Leu Tyr Val Ala Asn Ser Lys
850             855             860

Ser Ser Gly Lys Asp Tyr Gln Ala Lys Tyr Gly Gly Glu Phe Leu Ala
865             870             875             880

Glu Leu Lys Ala Lys Tyr Pro Glu Met Phe Lys Val Asn Met Ile Ser
            885             890             895

Thr Gly Lys Pro Ile Asp Asp Ser Val Lys Leu Lys Gln Trp Lys Ala
            900             905             910

Glu Tyr Phe Asn Gly Thr Asn Val Leu Glu Arg Gly Val Gly Tyr Val
            915             920             925

Leu Ser Asp Glu Ala Thr Gly Lys Tyr Phe Thr Val Thr Lys Glu Gly
930             935             940

Asn Phe Ile Pro Leu Gln Leu Thr Gly Lys Glu Lys Val Ile Thr Gly
945             950             955             960

Phe Ser Ser Asp Gly Lys Gly Ile Thr Tyr Phe Gly Thr Ser Gly Thr
            965             970             975

Gln Ala Lys Ser Ala Phe Val Thr Phe Asn Gly Asn Thr Tyr Tyr Phe
            980             985             990

Asp Ala Arg Gly His Met Val Thr Asn Ser Glu Tyr Ser Pro Asn Gly
            995             1000            1005

Lys Asp Val Tyr Arg Phe Leu Pro Asn Gly Ile Met Leu Ser Asn
    1010            1015            1020

Ala Phe Tyr Ile Asp Ala Asn Gly Asn Thr Tyr Leu Tyr Asn Ser
    1025            1030            1035
```

Lys Gly Gln Met Tyr Lys Gly Gly Tyr Thr Lys Phe Asp Val Ser
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Gly Ile Lys Asp Thr Trp Arg Asn Ile Asn Gly
    1115                1120                1125

Lys Trp Tyr Tyr Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Phe Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asn Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Leu Ala Tyr Pro Pro Arg
    1325                1330                1335

Val Leu Asn
    1340

<210> SEQ ID NO 2
<211> LENGTH: 1341
<212> TYPE: PRT
<213> ORGANISM: Streptococcus salivarius K12

<400> SEQUENCE: 2

Met Thr Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Ser Thr His Ser Phe Thr Pro Gly Thr

```
                  35                  40                  45
Thr Asn Ile Val Asp Gly Phe Ser Ile Asn Asn Arg Ala Tyr Asp Ser
 50                  55                  60
Ser Glu Ala Ser Phe Glu Leu Ile Asn Gly Tyr Leu Thr Ala Asp Ser
 65                  70                  75                  80
Trp Tyr Arg Pro Val Ser Ile Ile Lys Asp Gly Val Thr Trp Gln Ala
                     85                  90                  95
Ser Thr Ala Glu Asp Phe Arg Pro Leu Leu Met Ala Trp Trp Pro Asn
                 100                 105                 110
Val Asp Thr Gln Val Asn Tyr Leu Asn Tyr Met Ser Lys Val Phe Asn
             115                 120                 125
Leu Glu Ala Lys Tyr Thr Ser Thr Asp Lys Gln Ala Asp Leu Asn Arg
         130                 135                 140
Ala Ala Lys Asp Ile Gln Val Lys Ile Glu Gln Lys Ile Gln Ala Glu
145                 150                 155                 160
Lys Ser Thr Gln Trp Leu Arg Glu Thr Ile Ser Ala Phe Val Lys Thr
                 165                 170                 175
Gln Pro Gln Trp Asn Lys Glu Thr Glu Asn Tyr Ser Lys Gly Gly Gly
             180                 185                 190
Glu Asp His Leu Gln Gly Gly Ala Leu Leu Tyr Val Asn Asp Ser Arg
         195                 200                 205
Thr Pro Trp Ala Asn Ser Asn Tyr Arg Leu Leu Asn Arg Thr Ala Thr
210                 215                 220
Asn Gln Thr Gly Thr Ile Asn Lys Ser Val Leu Asp Glu Gln Ser Asp
225                 230                 235                 240
Pro Asn His Met Gly Gly Phe Asp Phe Leu Leu Ala Asn Asp Val Asp
                 245                 250                 255
Leu Ser Asn Pro Val Val Gln Ala Glu Gln Leu Asn Gln Ile His Tyr
             260                 265                 270
Leu Met Asn Trp Gly Ser Ile Val Met Gly Asp Lys Asp Ala Asn Phe
         275                 280                 285
Asp Gly Ile Arg Val Asp Ala Val Asp Asn Val Asn Ala Asp Met Leu
     290                 295                 300
Gln Leu Tyr Thr Asn Tyr Phe Arg Glu Tyr Tyr Gly Val Asn Lys Ser
305                 310                 315                 320
Glu Ala Gln Ala Leu Ala His Ile Ser Val Leu Glu Ala Trp Ser Leu
                 325                 330                 335
Asn Asp Asn His Tyr Asn Asp Lys Thr Asp Gly Ala Ala Leu Ala Met
             340                 345                 350
Glu Asn Lys Gln Arg Leu Ala Leu Leu Phe Ser Leu Ala Lys Pro Ile
         355                 360                 365
Lys Asp Arg Thr Pro Ala Val Ser Pro Leu Tyr Asn Asn Thr Phe Asn
     370                 375                 380
Thr Thr Gln Arg Asp Phe Lys Thr Asp Trp Ile Asn Lys Asp Gly Ser
385                 390                 395                 400
Thr Ala Tyr Asn Glu Asp Gly Thr Ala Lys Gln Ser Thr Ile Gly Lys
                 405                 410                 415
Tyr Asn Glu Lys Tyr Gly Asp Ala Ser Gly Asn Tyr Val Phe Ile Arg
             420                 425                 430
Ala His Asp Asn Asn Val Gln Asp Ile Ile Ala Glu Ile Ile Lys Lys
         435                 440                 445
Glu Ile Asn Lys Lys Ser Asp Gly Phe Thr Ile Ser Asp Ser Glu Met
     450                 455                 460
```

```
Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
        500                 505                 510

Asp Gly His Tyr Met Glu Thr Lys Ser Pro Tyr His Asp Thr Ile Val
    515                 520                 525

Asn Leu Met Lys Asn Arg Ile Lys Tyr Val Ser Gly Gly Gln Ala Gln
530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
        690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Asp His Ser Leu Tyr Val Ala Asn Ser Lys
        850                 855                 860

Ser Ser Gly Arg Asp Tyr Gln Ala Gln Tyr Gly Gly Glu Phe Leu Ala
865                 870                 875                 880
```

```
Glu Leu Lys Ala Lys Tyr Pro Lys Met Phe Thr Glu Asn Met Ile Ser
            885                 890                 895

Thr Gly Lys Pro Ile Asp Asp Ser Val Lys Leu Lys Gln Trp Lys Ala
        900                 905                 910

Lys Tyr Phe Asn Gly Thr Asn Val Leu Asp Arg Gly Val Gly Tyr Val
        915                 920                 925

Leu Ser Asp Glu Ala Thr Gly Lys Tyr Phe Val Thr Lys Glu Gly
    930                 935                 940

Asn Phe Ile Pro Leu Gln Leu Thr Gly Asn Glu Lys Ala Val Thr Gly
945                 950                 955                 960

Phe Ser Asn Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
            980                 985                 990

Asp Ala Arg Gly His Met Val Thr  Asn Gly Glu Tyr Ser  Pro Asn Gly
            995                 1000                1005

Lys Asp  Val Tyr Arg Phe Leu  Pro Asn Gly Ile Met  Leu Ser Asn
        1010                1015                1020

Ala Phe  Tyr Val Asp Ala Asn  Gly Asn Thr Tyr Leu  Tyr Asn Tyr
        1025                1030                1035

Lys Gly  Gln Met Tyr Lys Gly  Gly Tyr Thr Lys Phe  Asp Val Thr
        1040                1045                1050

Glu Thr  Asp Lys Asp Gly Asn  Glu Ser Lys Val Val  Lys Phe Arg
        1055                1060                1065

Tyr Phe  Thr Asn Glu Gly Val  Met Ala Lys Gly Leu  Thr Val Ile
        1070                1075                1080

Asp Gly  Ser Thr Gln Tyr Phe  Gly Glu Asp Gly Phe  Gln Thr Lys
        1085                1090                1095

Asp Lys  Leu Ala Thr Tyr Lys  Gly Lys Thr Tyr Tyr  Phe Glu Ala
        1100                1105                1110

His Thr  Gly Asn Ala Ile Lys  Asn Thr Trp Arg Asn  Ile Asp Gly
        1115                1120                1125

Lys Trp  Tyr His Phe Asp Glu  Asn Gly Val Ala Ala  Thr Gly Ala
        1130                1135                1140

Gln Val  Ile Asn Gly Gln Lys  Leu Tyr Phe Asn Glu  Asp Gly Ser
        1145                1150                1155

Gln Val  Lys Gly Gly Val Val  Lys Asn Ala Asp Gly  Thr Tyr Ser
        1160                1165                1170

Lys Tyr  Lys Glu Gly Ser Gly  Glu Leu Val Thr Asn  Glu Phe Phe
        1175                1180                1185

Thr Thr  Asp Gly Asn Val Trp  Tyr Tyr Ala Gly Ala  Asp Gly Lys
        1190                1195                1200

Thr Val  Thr Gly Ala Gln Val  Ile Asn Gly Gln His  Leu Tyr Phe
        1205                1210                1215

Lys Glu  Asp Gly Ser Gln Val  Lys Gly Gly Val Val  Lys Asn Ala
        1220                1225                1230

Asp Gly  Thr Tyr Ser Lys Tyr  Asp Ala Ala Thr Gly  Glu Arg Leu
        1235                1240                1245

Thr Asn  Glu Phe Phe Thr Thr  Gly Asp Asn Asn Trp  Tyr Tyr Ile
        1250                1255                1260

Gly Ser  Asn Gly Lys Thr Val  Thr Gly Glu Val Lys  Ile Gly Ala
        1265                1270                1275

Asp Thr  Tyr Tyr Phe Ala Lys  Asp Gly Lys Gln Val  Lys Gly Gln
```

```
              1280                1285                1290
Thr Val Thr Ala Gly Asn Gly Arg Ile Ser Tyr Tyr Tyr Gly Asp
        1295                1300                1305

Ser Gly Lys Lys Ala Ile Ser Thr Trp Ile Glu Ile Gln Pro Gly
    1310                1315                1320

Ile Tyr Val Tyr Phe Asp Lys Thr Gly Ile Ala Tyr Pro Pro Arg
    1325                1330                1335

Val Leu Asn
    1340

<210> SEQ ID NO 3
<211> LENGTH: 1341
<212> TYPE: PRT
<213> ORGANISM: Streptococcus salivarius SK126

<400> SEQUENCE: 3

Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
                35                  40                  45

Thr Asn Ile Val Asp Gly Phe Ser Ile Asn Asn Arg Ala Tyr Asp Ser
50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
                115                 120                 125

Leu Asp Ala Lys Tyr Ser Ser Thr Asp Lys Gln Glu Thr Leu Lys Val
                130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
                195                 200                 205

Thr Pro Trp Ala Asn Ser Asp Tyr Arg Arg Leu Asn Arg Thr Ala Thr
                210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
                275                 280                 285

Asp Gly Ile Arg Val Asp Ala Val Asp Asn Val Asp Ala Asp Met Leu
                290                 295                 300
```

-continued

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
            325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
            405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
            515                 520                 525

Asn Leu Met Lys Ser Arg Ile Lys Tyr Val Ser Gly Gly Gln Ala Gln
            530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
            565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
            595                 600                 605

Gln Ser Ala Lys Leu Asn Val Glu Met Gly Lys Ile His Ala Asn Gln
            610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
            645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
            675                 680                 685

Ser Asp Asp Gln Asp Ile Arg Val Ala Pro Ser Thr Glu Ala Lys Lys
            690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp

```
            725             730             735
Pro Ser Val Tyr Thr Asn Arg Lys Ile Ala Glu Asn Val Asp Leu Phe
        740             745             750
Lys Ser Trp Gly Val Thr Ser Phe Glu Met Ala Pro Gln Phe Val Ser
        755             760             765
Ala Asp Asp Gly Thr Phe Leu Asp Ser Val Ile Gln Asn Gly Tyr Ala
        770             775             780
Phe Ala Asp Arg Tyr Asp Leu Ala Met Ser Lys Asn Asn Lys Tyr Gly
785             790             795             800
Ser Lys Glu Asp Leu Arg Asp Ala Leu Lys Ala Leu His Lys Ala Gly
                805             810             815
Ile Gln Ala Ile Ala Asp Trp Val Pro Asp Gln Ile Tyr Gln Leu Pro
                820             825             830
Gly Lys Glu Val Val Thr Ala Thr Arg Thr Asp Gly Ala Gly Arg Lys
                835             840             845
Ile Ala Asp Ala Ile Ile Asp His Ser Leu Tyr Val Ala Asn Thr Lys
                850             855             860
Ser Ser Gly Lys Asp Tyr Gln Ala Lys Tyr Gly Gly Glu Phe Leu Ala
865             870             875             880
Glu Leu Lys Ala Lys Tyr Pro Glu Met Phe Lys Val Asn Met Ile Ser
                885             890             895
Thr Gly Lys Pro Ile Asp Asp Ser Val Lys Leu Lys Gln Trp Lys Ala
                900             905             910
Glu Tyr Phe Asn Gly Thr Asn Val Leu Glu Arg Gly Val Gly Tyr Val
                915             920             925
Leu Ser Asp Glu Ala Thr Gly Lys Tyr Phe Thr Val Thr Lys Asp Gly
                930             935             940
Asn Phe Ile Pro Leu Gln Leu Thr Gly Asn Glu Lys Val Val Thr Gly
945             950             955             960
Phe Ser Asn Asp Gly Lys Gly Ile Thr Tyr Phe Gly Thr Ser Gly Thr
                965             970             975
Gln Ala Lys Ser Ala Phe Val Thr Phe Asn Gly Asn Thr Tyr Tyr Phe
                980             985             990
Asp Ala Arg Gly His Met Val Thr Asn Gly Glu Tyr Ser Pro Asn Gly
                995             1000            1005
Lys Asp Val Tyr Arg Phe Leu Pro Asn Gly Ile Met Leu Ser Asn
    1010            1015            1020
Ala Phe Tyr Val Asp Ala Asn Gly Asn Thr Tyr Leu Tyr Asn Ser
    1025            1030            1035
Lys Gly Gln Met Tyr Lys Gly Gly Tyr Thr Lys Phe Asp Val Thr
    1040            1045            1050
Glu Thr Asp Lys Asp Gly Lys Glu Ser Lys Val Val Lys Phe Arg
    1055            1060            1065
Tyr Phe Thr Asn Glu Gly Val Met Ala Lys Gly Val Thr Val Ile
    1070            1075            1080
Asp Gly Phe Thr Gln Tyr Phe Gly Glu Asp Gly Phe Gln Ala Lys
    1085            1090            1095
Asp Lys Leu Val Thr Phe Lys Gly Lys Thr Tyr Tyr Phe Asp Ala
    1100            1105            1110
His Thr Gly Asn Ala Ile Lys Asp Thr Trp Arg Asn Ile Asn Gly
    1115            1120            1125
Lys Trp Tyr His Phe Asp Ala Asn Gly Val Ala Ala Thr Gly Ala
    1130            1135            1140
```

-continued

```
Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Ile Ala Tyr Pro Pro Arg
    1325                1330                1335

Val Leu Asn
    1340

<210> SEQ ID NO 4
<211> LENGTH: 1340
<212> TYPE: PRT
<213> ORGANISM: Streptococcus salivarius PS4

<400> SEQUENCE: 4

Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Gln Gly Thr
                35                  40                  45

Thr Asn Ile Val Asp Gly Phe Ser Lys Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Lys Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
                115                 120                 125

Leu Asp Ala Lys Tyr Thr Ser Thr Asp Lys Gln Val Asp Leu Asn Arg
                130                 135                 140

Ala Ala Lys Asp Ile Gln Val Lys Ile Glu Gln Lys Ile Gln Ala Glu
```

```
                145                 150                 155                 160
        Lys Ser Thr Gln Trp Leu Arg Glu Ala Ile Ser Ala Phe Val Lys Thr
                        165                 170                 175
        Gln Pro Gln Trp Asn Lys Glu Thr Glu Asn Phe Ser Lys Gly Gly Gly
                        180                 185                 190
        Glu Asp His Leu Gln Gly Gly Ala Leu Leu Tyr Val Asn Asp Pro Arg
                        195                 200                 205
        Thr Pro Trp Ala Asn Ser Asn Tyr Arg Leu Leu Asn Arg Thr Ala Thr
                        210                 215                 220
        Asn Gln Thr Gly Thr Ile Asp Lys Ser Val Leu Asp Glu Gln Ser Asp
        225                 230                 235                 240
        Pro Asn His Met Gly Gly Phe Asp Phe Leu Leu Ala Asn Asp Val Asp
                            245                 250                 255
        Thr Ser Asn Pro Val Val Gln Ala Glu Gln Leu Asn Gln Ile His Tyr
                        260                 265                 270
        Leu Met Asn Trp Gly Ser Ile Val Met Gly Asp Lys Asp Ala Asn Phe
                        275                 280                 285
        Asp Gly Ile Arg Val Asp Ala Val Asp Asn Val Asp Ala Asp Met Leu
                290                 295                 300
        Gln Leu Tyr Thr Asn Tyr Phe Arg Glu Tyr Tyr Gly Val Asn Lys Ser
        305                 310                 315                 320
        Glu Ala Asn Ala Leu Ala His Ile Ser Val Leu Glu Ala Trp Ser Leu
                        325                 330                 335
        Asn Asp Asn His Tyr Asn Asp Lys Thr Asp Gly Ala Ala Leu Ala Met
                        340                 345                 350
        Glu Asn Lys Gln Arg Leu Ala Leu Leu Phe Ser Leu Ala Lys Pro Ile
                        355                 360                 365
        Lys Glu Arg Thr Pro Ala Val Ser Pro Leu Tyr Asn Asn Thr Phe Asn
                        370                 375                 380
        Thr Thr Gln Arg Asp Glu Lys Thr Asp Trp Ile Asn Lys Asp Gly Ser
        385                 390                 395                 400
        Lys Ala Tyr Asn Glu Asp Gly Thr Val Lys Gln Ser Thr Ile Gly Lys
                        405                 410                 415
        Tyr Asn Glu Lys Tyr Gly Asp Ala Ser Gly Asn Tyr Val Phe Ile Arg
                        420                 425                 430
        Ala His Asp Asn Val Gln Asp Ile Ile Ala Glu Ile Ile Lys Lys
                        435                 440                 445
        Glu Ile Asn Pro Lys Ser Asp Gly Phe Thr Ile Thr Asp Ala Glu Met
                450                 455                 460
        Lys Lys Ala Phe Glu Ile Tyr Asn Lys Asp Met Leu Ser Ser Asp Lys
        465                 470                 475                 480
        Lys Tyr Thr Leu Asn Asn Ile Pro Ala Ala Tyr Ala Val Met Leu Gln
                        485                 490                 495
        Asn Met Glu Thr Ile Thr Arg Val Tyr Tyr Gly Asp Leu Tyr Thr Asp
                        500                 505                 510
        Asp Gly His Tyr Met Glu Thr Lys Ser Pro Tyr Tyr Asp Thr Ile Val
                        515                 520                 525
        Asn Leu Met Lys Asn Arg Ile Lys Tyr Val Ser Gly Gly Gln Ala Gln
                        530                 535                 540
        Arg Ser Tyr Trp Leu Pro Thr Asp Gly Lys Met Asp Lys Ser Asp Val
        545                 550                 555                 560
        Glu Leu Tyr Arg Thr Asn Glu Val Tyr Thr Ser Val Arg Tyr Gly Lys
                        565                 570                 575
```

```
Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Ser Leu Asp
        595                 600                 605

Lys Ser Ala Lys Leu Asp Val Glu Met Gly Lys Ile His Ala Asn Gln
    610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
    930                 935                 940

Asn Phe Ile Pro Leu Gln Leu Lys Gly Asn Glu Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990
```

```
Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Gly Val Val Lys Asn Ala Asp Gly Thr Phe Ser Lys
    1160                1165                1170

Tyr Lys Asp Gly Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Tyr Phe Gly Asp Ser
    1295                1300                1305

Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335

Met Asn
    1340

<210> SEQ ID NO 5
<211> LENGTH: 1340
<212> TYPE: PRT
<213> ORGANISM: Unknown
<220> FEATURE:
<223> OTHER INFORMATION: unknown Streptococcus sp. C150
```

<400> SEQUENCE: 5

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
```

```
            405                 410                 415
Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Glu Lys Ser Asp Gly Phe Thr Ile Thr Asp Ser Glu Met
    450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly Asn Tyr Met Glu Ala Lys Ser Pro Tyr Tyr Asp Thr Ile Val
            515                 520                 525

Asn Leu Met Lys Ser Arg Ile Lys Tyr Val Ser Gly Gly Gln Ala Gln
        530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Thr Leu Asp
            595                 600                 605

Gln Ser Ala Lys Leu Asn Val Val Met Gly Lys Ile His Ala Asn Gln
        610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
            675                 680                 685

Ser Asp Asp Gln Asp Ile Arg Val Ala Ala Ser Thr Ala Ala Lys Lys
        690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830
```

-continued

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Asp Arg Gly Val Gly Tyr Val
                915                 920                 925

Leu Ser Asp Glu Ala Thr Gly Lys Tyr Phe Thr Val Thr Lys Glu Gly
    930                 935                 940

Asn Phe Ile Pro Leu Gln Leu Lys Gly Asn Lys Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Ser Ile Val Lys Asn Ala Asp Gly Thr Phe Ser Lys
    1160                1165                1170

Tyr Lys Asp Ser Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Tyr Phe Gly Asp Ser
    1295                1300                1305

Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335

Met Asn
    1340

<210> SEQ ID NO 6
<211> LENGTH: 1477
<212> TYPE: PRT
<213> ORGANISM: Streptococcus salivarius

<400> SEQUENCE: 6

Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Thr Asn Thr Gln Ala Thr Ala Glu
    50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110

Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
    210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

```
Asn Tyr Met Ser Lys Val Phe Asn Leu Asp Ala Lys Tyr Ser Ser Thr
            260             265             270

Asp Lys Gln Glu Thr Leu Lys Val Ala Ala Lys Asp Ile Gln Ile Lys
        275             280             285

Ile Glu Gln Lys Ile Gln Ala Glu Lys Ser Thr Gln Trp Leu Arg Glu
290             295             300

Thr Ile Ser Ala Phe Val Lys Thr Gln Pro Gln Trp Asn Lys Glu Thr
305             310             315             320

Glu Asn Tyr Ser Lys Gly Gly Glu Asp His Leu Gln Gly Gly Ala
            325             330             335

Leu Leu Tyr Val Asn Asp Ser Arg Thr Pro Trp Ala Asn Ser Asp Tyr
            340             345             350

Arg Arg Leu Asn Arg Thr Ala Thr Asn Gln Thr Gly Thr Ile Asp Lys
        355             360             365

Ser Ile Leu Asp Glu Gln Ser Asp Pro Asn His Met Gly Gly Phe Asp
370             375             380

Phe Leu Leu Ala Asn Asp Val Asp Leu Ser Asn Pro Val Val Gln Ala
385             390             395             400

Glu Gln Leu Asn Gln Ile His Tyr Leu Met Asn Trp Gly Ser Ile Val
            405             410             415

Met Gly Asp Lys Asp Ala Asn Phe Asp Gly Ile Arg Val Asp Ala Val
            420             425             430

Asp Asn Val Asp Ala Asp Met Leu Gln Leu Tyr Thr Asn Tyr Phe Arg
        435             440             445

Glu Tyr Tyr Gly Val Asn Lys Ser Glu Ala Asn Ala Leu Ala His Ile
450             455             460

Ser Val Leu Glu Ala Trp Ser Leu Asn Asp Asn His Tyr Asn Asp Lys
465             470             475             480

Thr Asp Gly Ala Ala Leu Ala Met Glu Asn Lys Gln Arg Leu Ala Leu
            485             490             495

Leu Phe Ser Leu Ala Lys Pro Ile Lys Glu Arg Thr Pro Ala Val Ser
            500             505             510

Pro Leu Tyr Asn Asn Thr Phe Asn Thr Thr Gln Arg Asp Glu Lys Thr
            515             520             525

Asp Trp Ile Asn Lys Asp Gly Ser Lys Ala Tyr Asn Glu Asp Gly Thr
        530             535             540

Val Lys Gln Ser Thr Ile Gly Lys Tyr Asn Glu Lys Tyr Gly Asp Ala
545             550             555             560

Ser Gly Asn Tyr Val Phe Ile Arg Ala His Asp Asn Asn Val Gln Asp
            565             570             575

Ile Ile Ala Glu Ile Ile Lys Lys Glu Ile Asn Pro Lys Ser Asp Gly
            580             585             590

Phe Thr Ile Thr Asp Ala Glu Met Lys Gln Ala Phe Glu Ile Tyr Asn
        595             600             605

Lys Asp Met Leu Ser Ser Asp Lys Lys Tyr Thr Leu Asn Asn Ile Pro
        610             615             620

Ala Ala Tyr Ala Val Met Leu Gln Asn Met Glu Thr Ile Thr Arg Val
625             630             635             640

Tyr Tyr Gly Asp Leu Tyr Thr Asp Asp Gly His Tyr Met Glu Thr Lys
            645             650             655

Ser Pro Tyr Tyr Asp Thr Ile Val Asn Leu Met Lys Ser Arg Ile Lys
            660             665             670
```

```
Tyr Val Ser Gly Gly Gln Ala Gln Arg Ser Tyr Trp Leu Pro Thr Asp
            675                 680                 685

Gly Lys Met Asp Asn Ser Asp Val Glu Leu Tyr Arg Thr Asn Glu Val
        690                 695                 700

Tyr Thr Ser Val Arg Tyr Gly Lys Asp Ile Met Thr Ala Asn Asp Thr
705                 710                 715                 720

Glu Gly Ser Lys Tyr Ser Arg Thr Ser Gly Gln Val Thr Leu Val Ala
                725                 730                 735

Asn Asn Pro Lys Leu Asn Leu Asp Gln Ser Ala Lys Leu Asn Val Glu
            740                 745                 750

Met Gly Lys Ile His Ala Asn Gln Lys Tyr Arg Ala Leu Ile Val Gly
            755                 760                 765

Thr Ala Asp Gly Ile Lys Asn Phe Thr Ser Asp Ala Asp Ala Ile Ala
770                 775                 780

Ala Gly Tyr Val Lys Glu Thr Asp Ser Asn Gly Val Leu Thr Phe Gly
785                 790                 795                 800

Ala Asn Asp Ile Lys Gly Tyr Glu Thr Phe Asp Met Ser Gly Phe Val
                805                 810                 815

Ala Val Trp Val Pro Val Gly Ala Ser Asp Asn Gln Asp Ile Arg Val
                820                 825                 830

Ala Pro Ser Thr Glu Ala Lys Lys Glu Gly Leu Thr Leu Lys Ala
            835                 840                 845

Thr Glu Ala Tyr Asp Ser Gln Leu Ile Tyr Glu Gly Phe Ser Asn Phe
850                 855                 860

Gln Thr Ile Pro Asp Gly Ser Asp Pro Ser Val Tyr Thr Asn Arg Lys
865                 870                 875                 880

Ile Ala Glu Asn Val Asp Leu Phe Lys Ser Trp Gly Val Thr Ser Phe
                885                 890                 895

Glu Met Ala Pro Gln Phe Val Ser Ala Asp Asp Gly Thr Phe Leu Asp
                900                 905                 910

Ser Val Ile Gln Asn Gly Tyr Ala Phe Ala Asp Arg Tyr Asp Leu Ala
            915                 920                 925

Met Ser Lys Asn Asn Lys Tyr Gly Ser Lys Glu Asp Leu Arg Asp Ala
930                 935                 940

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Glu Val Val Thr Ala Thr
                965                 970                 975

Arg Thr Asp Gly Ala Gly Arg Lys Ile Ala Asp Ala Ile Asp His
            980                 985                 990

Ser Leu Tyr Val Ala Asn Ser Lys  Ser Ser Gly Lys Asp  Tyr Gln Ala
            995                 1000                1005

Lys Tyr Gly Gly Glu Phe Leu  Ala Glu Leu Lys Ala  Lys Tyr Pro
    1010                1015                1020

Glu Met Phe Lys Val Asn Met  Ile Ser Thr Gly Lys  Pro Ile Asp
    1025                1030                1035

Asp Ser Val Lys Leu Lys Gln  Trp Lys Ala Glu Tyr  Phe Asn Gly
    1040                1045                1050

Thr Asn Val Leu Glu Arg Gly  Val Gly Tyr Val Leu  Ser Asp Glu
    1055                1060                1065
```

```
Ala Thr Gly Lys Tyr Phe Thr Val Thr Lys Glu Gly Asn Phe Ile
    1070            1075                1080

Pro Leu Gln Leu Thr Gly Lys Glu Lys Val Ile Thr Gly Phe Ser
    1085            1090                1095

Ser Asp Gly Lys Gly Ile Thr Tyr Phe Gly Thr Ser Gly Thr Gln
    1100            1105                1110

Ala Lys Ser Ala Phe Val Thr Phe Asn Gly Asn Thr Tyr Tyr Phe
    1115            1120                1125

Asp Ala Arg Gly His Met Val Thr Asn Ser Glu Tyr Ser Pro Asn
    1130            1135                1140

Gly Lys Asp Val Tyr Arg Phe Leu Pro Asn Gly Ile Met Leu Ser
    1145            1150                1155

Asn Ala Phe Tyr Ile Asp Ala Asn Gly Asn Thr Tyr Leu Tyr Asn
    1160            1165                1170

Ser Lys Gly Gln Met Tyr Lys Gly Gly Tyr Thr Lys Phe Asp Val
    1175            1180                1185

Ser Glu Thr Asp Lys Asp Gly Lys Glu Ser Lys Val Val Lys Phe
    1190            1195                1200

Arg Tyr Phe Thr Asn Glu Gly Val Met Ala Lys Gly Val Thr Val
    1205            1210                1215

Ile Asp Gly Phe Thr Gln Tyr Phe Gly Glu Asp Gly Phe Gln Ala
    1220            1225                1230

Lys Asp Lys Leu Val Thr Phe Lys Gly Lys Thr Tyr Tyr Phe Asp
    1235            1240                1245

Ala His Thr Gly Asn Gly Ile Lys Asp Thr Trp Arg Asn Ile Asn
    1250            1255                1260

Gly Lys Trp Tyr Tyr Phe Asp Ala Asn Gly Val Ala Ala Thr Gly
    1265            1270                1275

Ala Gln Val Ile Asn Gly Gln Lys Leu Tyr Phe Asn Glu Asp Gly
    1280            1285                1290

Ser Gln Val Lys Gly Gly Val Val Lys Asn Ala Asp Gly Thr Tyr
    1295            1300                1305

Ser Lys Tyr Lys Glu Gly Phe Gly Glu Leu Val Thr Asn Glu Phe
    1310            1315                1320

Phe Thr Thr Asp Gly Asn Val Trp Tyr Tyr Ala Gly Ala Asn Gly
    1325            1330                1335

Lys Thr Val Thr Gly Ala Gln Val Ile Asn Gly Gln His Leu Tyr
    1340            1345                1350

Phe Asn Ala Asp Gly Ser Gln Val Lys Gly Gly Val Val Lys Asn
    1355            1360                1365

Ala Asp Gly Thr Tyr Ser Lys Tyr Asn Ala Ser Thr Gly Glu Arg
    1370            1375                1380

Leu Thr Asn Glu Phe Phe Thr Gly Asp Asn Trp Tyr Tyr
    1385            1390                1395

Ile Gly Ala Asn Gly Lys Ser Val Thr Gly Glu Val Lys Ile Gly
    1400            1405                1410

Asp Asp Thr Tyr Phe Phe Ala Lys Asp Gly Lys Gln Val Lys Gly
    1415            1420                1425

Gln Thr Val Ser Ala Gly Asn Gly Arg Ile Ser Tyr Tyr Tyr Gly
    1430            1435                1440

Asp Ser Gly Lys Arg Ala Val Ser Thr Trp Ile Glu Ile Gln Pro
    1445            1450                1455
```

-continued

```
Gly Val  Tyr Val Tyr Phe Asp  Lys Asn Gly Leu Ala  Tyr Pro Pro
    1460             1465             1470

Arg Val  Leu Asn
    1475
```

PRODUCTION AND COMPOSITION OF FRUCTOSE SYRUP

FIELD

This disclosure is in the field of saccharides. For example, this disclosure pertains to the production of compositions comprising a high fructose content.

REFERENCE TO SEQUENCE LISTING SUBMITTED ELECTRONICALLY

The official copy of the sequence listing is submitted electronically via EFS-Web as an ASCII formatted sequence listing with a file named 20151211_CL6456USNP_SequenceListing_ST25 created on Dec. 10, 2015, and having a size of 71 kilobytes and is filed concurrently with the specification. The sequence listing contained in this ASCII-formatted document is part of the specification and is herein incorporated by reference in its entirety.

BACKGROUND

Fructose syrup (FS) such as high fructose corn syrup (HFCS) is commonly employed as a sweetener, in part since it is easier to handle than granulated sugar. Starch and table sugar (sucrose) represent the most common feedstocks for producing FS.

Processes for producing FS from starch begin by hydrolyzing this polymer to its monomer, glucose. The glucose is then treated with a glucose isomerase enzyme to convert the glucose to fructose, up to an approximately 50:50 mixture on a dry basis. The isomerization typically yields a syrup ("F42") containing about 42% (dry weight basis [dwb]) fructose, at least about 50% (dwb) glucose, and a small fraction of oligosaccharides. The end point for the isomerization is selected to optimize the process economics. The fructose fraction of the F42 syrup is then enriched by chromatography to yield a syrup ("F90") containing roughly 90% (dwb) fructose. The glucose-enriched fraction from the F42 syrup is recycled and further isomerized into fructose, which is then fractionated by chromatography to increase the overall amount of F90 syrup produced. F90 syrup is typically blended with F42 syrup to produce commercial sweeteners such as HFCS 55, which contains about 55% fructose (dwb), at least about 40% (dwb) glucose, and a small fraction of oligosaccharides.

Processes for producing FS from sucrose involve inverting this disaccharide to glucose and fructose using an immobilized invertase enzyme. The glucose and fructose are then fractionated by chromatography to yield a FS containing at least 90% (dwb) fructose. The glucose fraction is isomerized to F42 using an immobilized glucose isomerase and then further fractionated by chromatography to increase the overall amount of high purity fructose produced.

However, the chromatographic purification steps involved in producing FS from starch and sucrose feedstock are expensive and capital-intensive due to the large amount of evaporation required.

Other processes involving enzymatic approaches have been disclosed attempting to produce FS, but have fallen short in certain respects. U.S. Patent Appl. Publ. No. 2009/0123603, for example, appears to disclose using alternan sucrase to produce a syrup containing about 40% (dwb) fructose from sucrose feedstock. This low fructose level, coupled with the presence of soluble alternan polymer, would necessitate further processing in order to obtain a more useful FS. As additional examples, U.S. Pat. Nos. 8,828,689 and 8,962,282 disclose enzymatic production of fructose-comprising aqueous compositions. Such compositions, however, are not suitable for use in food applications given the presence of borate therein. Also, though U.S. Pat. No. 6,242,225 discloses enzymatic production of fructose, it is believed this process is limited to producing compositions with fructose and byproduct levels unsuitable for use as FS.

Thus, new processes for enzymatic production of FS are sought that require less processing steps and/or additives. To that end, disclosed herein is FS comprising at least 55% (dwb) fructose and production methods thereof employing a glucosyltransferase reaction.

SUMMARY

In one embodiment, the present disclosure concerns a method for producing an aqueous composition comprising fructose, the method comprising:
(a) contacting water, sucrose, and a glucosyltransferase enzyme that synthesizes poly alpha-1,3-glucan having at least 30% alpha-1,3-linkages to produce a soluble fraction and an insoluble fraction, wherein the insoluble fraction comprises the poly alpha-1,3-glucan, and further wherein the soluble fraction comprises at least about 55% fructose on a dry weight basis, and
(b) separating the soluble fraction from the insoluble fraction, thereby providing an aqueous composition comprising fructose.

In another embodiment, the glucosyltransferase enzyme synthesizes poly alpha-1,3-glucan having at least 95% alpha-1,3-linkages.

In another embodiment, the soluble fraction further comprises soluble oligosaccharides with a degree of polymerization (DP) of 2 to about 15.

In another embodiment, the soluble fraction comprises less than about 30% of the soluble oligosaccharides on a dry weight basis.

In another embodiment, the method further comprises contacting the soluble fraction with an alpha-glucosidase enzyme to hydrolyze at least one glycosidic linkage of the oligosaccharides, thereby increasing the monosaccharide content in the soluble fraction.

In another embodiment, the soluble fraction comprises at least about 75% fructose on a dry weight basis.

In another embodiment, the method further comprises a process step that increases the content of monosaccharides relative to the content of other saccharides in the soluble fraction, wherein the process step optionally is nanofiltration or enzymatic hydrolysis.

In another embodiment, the method does not comprise chromatography as a process step to increase the content of fructose relative to the content of other saccharides in the soluble fraction Another embodiment of the present disclosure concerns an aqueous composition produced by a method herein, such as any of the above embodiments. In another embodiment, such an aqueous composition is comprised within, or is, an ingestible product, and optionally is used as a sweetener of the ingestible product.

Another embodiment of the present disclosure concerns an aqueous composition comprising: (i) at least about 55% fructose on a dry weight basis, (ii) about 3% to about 24% glucose on a dry weight basis, and (iii) soluble oligosaccharides with a degree of polymerization (DP) of 2 to about 15, wherein the oligosaccharides comprise glucose and/or fructose.

In another embodiment of the aqueous composition, the soluble oligosaccharides are selected from the group consisting of sucrose, leucrose, trehalulose, isomaltulose, maltulose, isomaltose, and nigerose.

In another embodiment of the aqueous composition, the oligosaccharides comprise (i) at least about 90 wt % glucose, and (ii) about 60-99% alpha-1,3 and about 1-40% alpha-1,6 glucosidic linkages.

In another embodiment, the aqueous composition comprises at least about 75% fructose on a dry weight basis.

In another embodiment, the aqueous composition comprises less than about 30% of the soluble oligosaccharides on a dry weight basis.

In another embodiment, the aqueous composition is comprised within, or is, an ingestible product, and optionally is used as a sweetener of the ingestible product.

In another embodiment, the aqueous composition has a conductivity less than about 50 µS/cm at about 30 wt % dry solids and an ICUMSA value less than about 50.

Another embodiment of the present disclosure concerns an ingestible product comprising an aqueous composition produced by a method herein, wherein the ingestible product is a food, beverage, animal feed, human or animal nutritional product, pharmaceutical product, or oral care product.

BRIEF DESCRIPTION OF THE DRAWINGS AND SEQUENCES

TABLE 1

Summary of Protein SEQ ID Numbers

Figure 1:
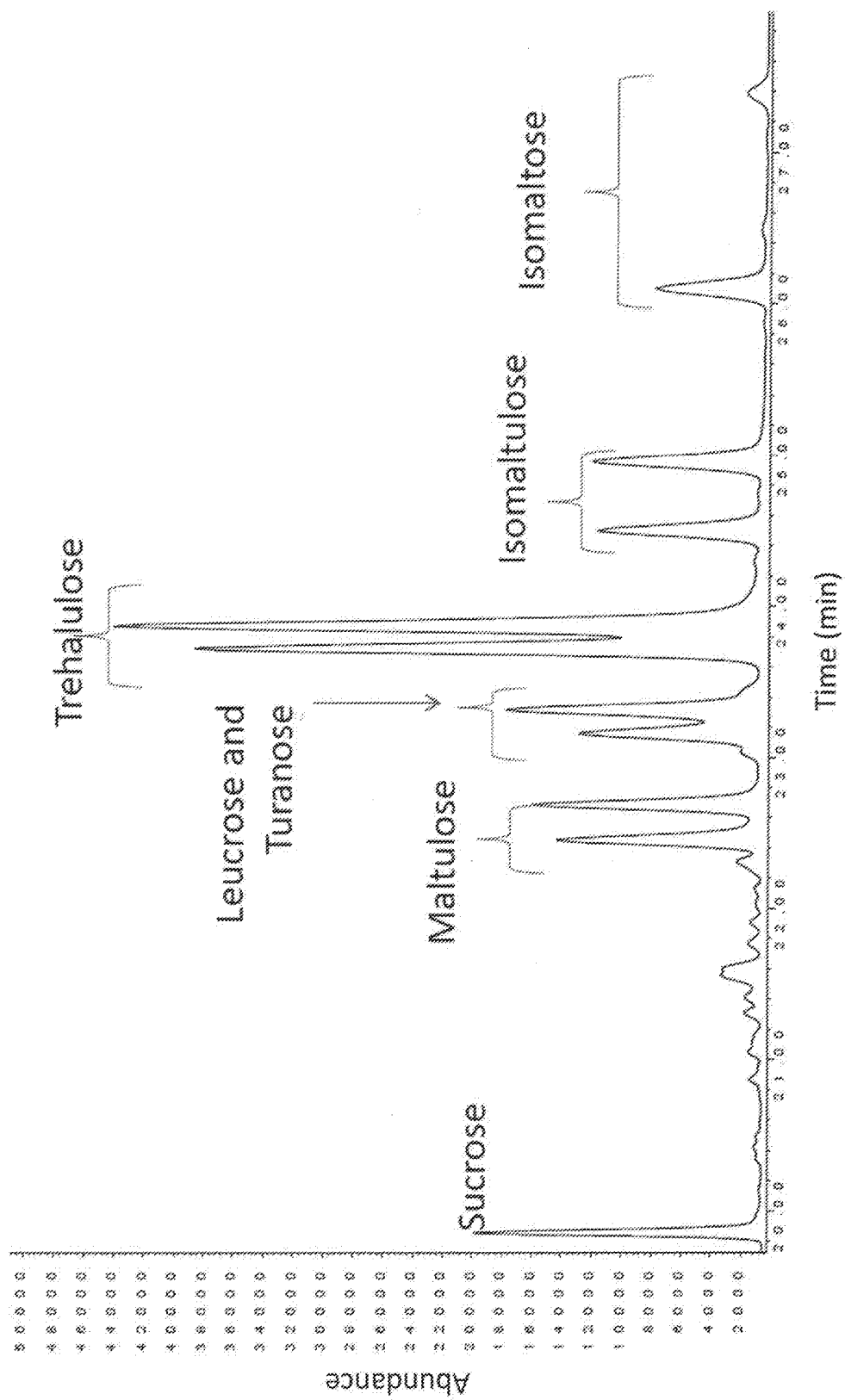
FIG. 1 shows a distribution of disaccharides present in the hydrolyzed fructose syrup of Table 6, as detected by gas chromatography-mass spectroscopy.

| Description | Protein SEQ ID NO. |
|---|---|
| "GTF 7527" (short version of GTFJ), *Streptococcus salivarius*. The first 178 amino acids of the protein are deleted compared to GENBANK Identification No. 47527; a start methionine is included. | 1 (1341 aa) |
| "GTF 2678", *Streptococcus salivarius* K12. The first 188 amino acids of the protein are deleted compared to GENBANK Identification No. 400182678; a start methionine is included. | 2 (1341 aa) |
| "GTF 6855", *Streptococcus salivarius* SK126. The first 178 amino acids of the protein are deleted compared to GENBANK Identification No. 228476855; a start methionine is included. | 3 (1341 aa) |
| "GTF 2919", *Streptococcus salivarius* PS4. The first 92 amino acids of the protein are deleted compared to GENBANK Identification No. 383282919; a start methionine is included. | 4 (1340 aa) |
| "GTF 2765", unknown *Streptococcus* sp. C150. The first 193 amino acids of the protein are deleted compared to GENBANK Identification No. 322372765; a start methionine is included. | 5 (1340 aa) |
| GTFJ, *Streptococcus salivarius*. The first 42 amino acids of the protein are deleted compared to GENBANK Identification No. 47527; a start methionine is included. | 6 (1477 aa) |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The term "saccharide" as used herein refers to monosaccharides and/or disaccharides/oligosaccharides, unless otherwise noted. A "disaccharide" herein refers to a carbohydrate having two monosaccharides joined by a glycosidic linkage. An "oligosaccharide" herein refers to a carbohydrate that having 2 to 15 monosaccharides, for example, joined by glycosidic linkages. An oligosaccharide can also be referred to as an "oligomer". Monosaccharides (e.g., glucose, fructose) comprised within disaccharides/oligosaccharides can be referred to as "monomer units", "monosaccharide units", or other like terms. The terms "fructose" and "fructose content" herein refer to free fructose, unless otherwise disclosed (this logic similarly applies to other saccharides including glucose).

The terms "alpha-glucan", "alpha-glucan polymer" and the like are used interchangeably herein. An alpha-glucan is a polymer comprising glucose monomeric units linked together by alpha-glucosidic linkages. Poly alpha-1,3-glucan is an example of an alpha-glucan.

The terms "poly alpha-1,3-glucan", "alpha-1,3-glucan polymer", "glucan polymer" and the like are used interchangeably herein. Poly alpha-1,3-glucan is a polymer comprising glucose monomeric units linked together by glucosidic linkages, wherein at least about 30% of the glucosidic linkages are alpha-1,3-glucosidic linkages. Poly alpha-1,3-glucan in certain embodiments comprises at least 95% alpha-1,3-glucosidic linkages.

The terms "glycosidic linkage", "glycosidic bond" and the like are used interchangeably herein and refer to the covalent bond that joins a carbohydrate molecule to another carbohydrate molecule. The terms "glucosidic linkage", "glucosidic bond" and the like are used interchangeably herein and refer to a glycosidic linkage between two glucose molecules. The term "alpha-1,3-glucosidic linkage" as used herein refers to the type of covalent bond that joins alpha-D-glucose molecules to each other through carbons 1 and 3 on adjacent alpha-D-glucose rings. The term "alpha-1,6-glucosidic linkage" as used herein refers to the covalent bond that joins alpha-D-glucose molecules to each other through carbons 1 and 6 on adjacent alpha-D-glucose rings. Herein, "alpha-D-glucose" is referred to as "glucose." All glucosidic linkages disclosed herein are alpha-glucosidic linkages, except as otherwise noted.

The glycosidic linkage profile of an alpha-glucan herein can be determined using any method known in the art. For example, a linkage profile can be determined using methods that use nuclear magnetic resonance (NMR) spectroscopy (e.g., $^{13}C$ NMR or $^1H$ NMR). These and other methods that can be used are disclosed in Food *Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of poly alpha-1,3-glucan herein can be represented as weight-average molecular weight (Mw) or number-average molecular weight (Mn), the units of which are in Daltons or grams/mole. Alternatively, molecular weight can be represented as DPw (weight average degree of polymerization) or DPn (number average degree of polymerization). Various means are known in the art for calculating these molecular weight measurements such as with high-pressure liquid chromatography (HPLC), size exclusion chromatography (SEC), or gel permeation chromatography (GPC).

The degree of polymerization (DP) number of an oligosaccharide herein refers to the number of monomeric units in the oligosaccharide. For example, a DP3 oligosaccharide has 3 monomeric units.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "leucrose" and "D-glucopyranosyl-alpha(1-5)-D-fructopyranose" are used interchangeably herein and refer to a disaccharide containing an alpha-1,5 glucosyl-fructose linkage.

The term "trehalulose" as used herein refers to the disaccharide 1-O-alpha-D-glucopyranosyl-beta-D-fructose.

The term "isomaltulose" as used herein refers to the disaccharide 6-O-alpha-D-glucopyranosyl-D-fructose.

The term "maltulose" as used herein refers to the disaccharide 4-O-alpha-D-glucopyranosyl-D-fructose.

The term "isomaltose" as used herein refers to the disaccharide 6-O-alpha-D-glucopyranosyl-D-glucose.

The term "nigerose" as used herein refers to the disaccharide 3-O-alpha-D-glucopyranosyl-D-glucose.

The term "turanose" as used herein refers to the disaccharide 3-O-alpha-D-glucopyranosyl-D-fructose.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (byproducts) of a glucosyltransferase reaction can include glucose and various soluble oligosaccharides (e.g., DP2-DP7) including leucrose. Wild type forms of glucosyltransferase enzymes generally contain (in the N-terminal to C-terminal direction) a signal peptide, a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The term "glucosyltransferase catalytic domain" herein refers to the domain of a glucosyltransferase enzyme that provides alpha-glucan-synthesizing activity to a glucosyltransferase enzyme. A glucosyltransferase catalytic domain preferably does not require the presence of any other domains to have this activity.

The terms "enzymatic reaction", "glucosyltransferase reaction", "glucan synthesis reaction", "reaction composition" and the like are used interchangeably herein and generally refer to a reaction that initially comprises water, sucrose, at least one active glucosyltransferase enzyme, and optionally other components. Components that can be further present in a glucosyltransferase reaction typically after it has commenced include fructose, glucose, soluble oligosaccharides (e.g., DP2-DP7) such as leucrose, and soluble and/or insoluble alpha-glucan product(s) of DP8 or higher (e.g., DP100 and higher). It would be understood that certain glucan products, such as poly alpha-1,3-glucan with a degree of polymerization (DP) of at least 8 or 9, are water-insoluble and thus not dissolved in a glucan synthesis reaction, but rather may be present out of solution. It is in a glucan synthesis reaction where the step of contacting water, sucrose and a glucosyltransferase enzyme is performed. The term "under suitable reaction conditions" as used herein refers to reaction conditions that support conversion of sucrose to poly alpha-1,3-glucan via glucosyltransferase enzyme activity. An enzymatic reaction herein is not believed to occur in nature.

The term "aqueous composition" herein refers to an aqueous solution comprising at least about 55% fructose on a dry weight basis. A solid material that is not dissolved in the aqueous solution may optionally be present therein (i.e., an aqueous solution may itself be part of a mixture, for example). A soluble fraction herein is an example of an aqueous composition. The solvent of an aqueous composition comprises about, or at least about 70, 75, 80, 85, 90, 95, or 100 wt % water (or any integer value between 70 and 100 wt %), for example.

The term "soluble fraction" herein refers to a solution portion of a glucan synthesis reaction that has produced insoluble poly alpha-1,3-glucan. A soluble fraction can be a portion of, or all of, the solution of a glucan synthesis reaction, and typically has been (or will be) separated from an insoluble poly alpha-1,3-glucan product synthesized in the reaction. A soluble fraction herein comprises at least 55% fructose on a dry weight basis. An example of a soluble fraction is a filtrate of a glucan synthesis reaction. A soluble fraction can contain dissolved sugars such as sucrose, fructose, glucose, and soluble oligosaccharides (e.g., DP2-DP7) such as leucrose. Thus, a soluble fraction can optionally be referred to as a "fructose stream", "fructose syrup", or "sugar solution". The term "hydrolyzed fraction" and the like herein refer to a soluble fraction that has been treated with an alpha-glucosidase herein to hydrolyze leucrose and/or oligosaccharides present in the soluble fraction.

The term "insoluble fraction" herein refers to insoluble poly alpha-1,3-glucan formed in a glucan synthesis reaction. Other components, such as impurities, can optionally be comprised within an insoluble fraction herein (e.g., colorants).

The terms "dry weight basis" (dwb), "dry solids basis" (dsb) and the like are used interchangeably herein. The amount of a material (e.g., fructose) on a dry weight basis in a soluble fraction, for example, refers to the weight percentage of the material as it exists in all the dissolved material (e.g., fructose, sucrose, glucose, soluble DP2-7 oligosaccharides, optionally salts and impurities) in the soluble fraction. For example, if a soluble fraction comprises 75% (dwb) fructose, there would be 75 wt % fructose in the dry matter resulting from removing all the water from the soluble fraction.

The "percent dry solids" (percent DS) of a solution herein (e.g., soluble fraction, aqueous composition) refers to the wt % of all the materials (i.e., the solids) dissolved in the solution. For example, a 100 g solution with 10 wt % DS comprises 10 g of dissolved material.

The "yield" of poly alpha-1,3-glucan by a glucan synthesis reaction herein represents the weight of poly alpha-1,3-glucan product expressed as a percentage of the weight of sucrose substrate that is converted in the reaction. For example, if 100 g of sucrose in a reaction solution is converted to products, and 10 g of the products is poly alpha-1,3-glucan, the yield of the poly alpha-1,3-glucan would be 10%. This yield calculation can be considered as a measure of selectivity of the reaction toward poly alpha-1,3-glucan.

An "ICUMSA" (International Commission for Uniform Methods of Sugar Analysis) value, or "standard ICUMSA" value, is an international unit for expressing the purity of a sugar sample in solution, and is directly related to the color of the dissolved sugar. The greater the ICUMSA value of a sugar sample, the darker the sugar sample is. Methods of determining ICUMSA values for sugar samples are well known in the art and are disclosed by the International Commission for Uniform Methods of Sugar Analysis in *ICUMSA Methods of Sugar Analysis: Official and Tentative Methods Recommended by the International Commission for Uniform Methods of Sugar Analysis (ICUMSA)* (Ed. H. C. S. de Whalley, Elsevier Pub. Co., 1964), for example, which is incorporated herein by reference. ICUMSA can be measured, for example, by ICUMSA Method GS1/3-7 as described by R. J. McCowage, R. M. Urquhart and M. L. Burge (*Determination of the Solution Colour of Raw Sugars, Brown Sugars and Coloured Syrups at pH 7.0-Official*, Verlag Dr Albert Bartens, 2011 revision), which is incorporated herein by reference. ICUMSA values can be expressed in "reference base units" (RBU), for example. ICUMSA values herein can be measured, for example, following ICUMSA Method GS1/3-7 or the protocol provided in Table 2. For example, an ICUMSA value of a fructose syrup (soluble fraction) herein can be measured by at least (i) diluting about 3 g of the syrup in about 7 g of water, (ii) adjusting the pH of the diluted syrup to about 7.0 (e.g., using 0.1 M NaOH or 0.1M HCl), (iii) filtering the diluted syrup (e.g., with a ~0.45-micron filter), (iv) measuring the Brix (g solid/100 g) of the diluted syrup, (v) measuring the density (g/m L) of the diluted syrup, (vi) calculating the concentration, c, (g solid/mL) of the diluted syrup (i.e., Brix×density/100), (vii) measuring the absorbance, As, at about 420 nm using pathlength, b, in cm, (viii), and (ix) calculating ICUMSA as 1000×As/(b×c).

The terms "conductivity", "electrical conductivity" and the like are used interchangeably herein. Conductivity generally refers to the ability of an aqueous solution to conduct an electric current between two electrodes at a particular temperature and/or pH. Since a current flows by ion transport in solution, the higher the level of salts dissolved in an aqueous solution, the greater the conductivity of the solution. Thus, conductivity can be used herein to gauge the level ash (i.e., inorganic components) in a sugar solution herein. A suitable unit of measurement for conductivity herein is microSiemens per centimeter (µS/cm), and can be measured using a standard conductivity meter. In general, in order for a sugar solution to be suitable as a sweetener, it should have a conductivity below about 50 µS/cm. The conductivity of a sugar solution herein can be measured following any method known in the art, such as methodology disclosed in U.S. Pat. No. 8,097,086, which is incorporated herein by reference.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "alpha-glucosidase", "alpha-1,4-glucosidase", and "alpha-D-glucoside glucohydrolase" are used interchangeably herein. Alpha-glucosidases (EC 3.2.1.20) ("EC" refers to Enzyme Commission number) have previously been recognized as enzymes that catalyze hydrolytic release of terminal, non-reducing (1,4)-linked alpha-D-glucose residues from oligosaccharide (e.g., disaccharide) and polysaccharide substrates. Alpha-glucosidases also have hydrolytic activity toward alpha-1,5 glucosyl-fructose linkages, and toward alpha-1,3 and alpha-1,6 glucosyl-glucose linkages (refer to U.S. Patent Appl. Publ. Nos. 2015/0240278 and 2015/0240279). Transglucosidase and glucoamylase enzymes are examples of alpha-glucosidases with such activity.

The terms "transglucosidase" (TG), "transglucosidase enzyme", and "1,4-alpha-glucan 6-alpha-glucosyltransferase" are used interchangeably herein. Transglucosidases (EC 2.4.1.24) are D-glucosyltransferase enzymes that catalyze both hydrolytic and transfer reactions on incubation with certain alpha-D-gluco-oligosaccharides. Transglucosidases also have hydrolytic activity toward alpha-1,5 glucosyl-fructose linkages, and toward alpha-1,3 and alpha-1,6 glucosyl-glucose linkages.

The terms "glucoamylase" (GA), "glucoamylase enzyme", and "alpha-1,4-glucan glucohydrolase" are used interchangeably herein. Glucoamylases (EC 3.2.1.3) are exo-acting enzymes that catalyze hydrolysis of both alpha-1,4 and alpha-1,6 glycosidic linkages from non-reducing ends of glucose-containing di-, oligo- and poly-saccharides. Glucoamylases also have hydrolytic activity toward alpha-1,5 glucosyl-fructose linkages.

The term "hydrolysis" herein refers to a process in which the glycosidic linkages of an disaccharide/oligosaccharide are broken in a reaction involving water, thereby producing the constituent monosaccharides of the disaccharide/oligosaccharide. The term "enzymatic hydrolysis" herein can refer to, for example, a process in which an alpha-glucosidase is contacted with a soluble fraction to catalyze hydrolysis of leucrose and/or other oligosaccharides dissolved therein. The term "saccharification" herein refers to a process of breaking a saccharide (disaccharide/oligosaccharide) into its monosaccharide components. A saccharide can be saccharified in a hydrolysis reaction herein.

The term "nanofiltration" as used herein refers to the filtration process in which a low to moderately high pressure (typically 5-30 bar) transports solvent and some solutes through a semi-permeable membrane with some solutes being retained. A semi-permeable membrane for nanofiltration herein typically has pore sizes between 0.1 nm to 10 nm and/or molecular weight cut-off (MWCO) between 100-5000 Daltons and/or magnesium sulfate rejection between 50-99% (e.g., at a pressure of 9 bar, 2000 ppm feed concentration, 25° C.). Generally, the nanofiltration range is between "loose" reverse osmosis (RO) and "tight" ultrafiltration (UF). The material that passes through the membrane of a nanofiltration unit can be referred to as "permeate", whereas the material that does not pass through the membrane can be referred to as either "concentrate" or "retentate".

The terms "ingestible product" and "ingestible composition" are used interchangeably herein, and refer to any substance that, either alone or together with another substance, may be taken orally (i.e., by mouth) whether intended for consumption or not. Thus, an ingestible product includes food/beverage products, as well as otherwise non-edible products that can be used orally. "Food/beverage products" refer to any edible product intended for consumption (e.g., for nutritional purposes) by humans or animals, including solids, semi-solids, or liquids. "Non-edible products" ("non-edible compositions") refer to any composition that can be taken by the mouth for purposes other than food or beverage consumption. Examples of non-edible products herein include supplements, nutraceuticals, functional food products, pharmaceutical products, oral care products (e.g., dentifrices, mouthwashes), and cosmetic products such as sweetened lip balms.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining percent complementarity of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence may have the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. Any polypeptide amino acid sequence disclosed herein beginning with a methionine can optionally be considered without this methionine residue (i.e., a polypeptide sequence can be referred to in reference to the position-2 residue to the C-terminal residue of the sequence).

All the amino acid residues at each amino acid position of the proteins disclosed herein are examples. Given that certain amino acids share similar structural and/or charge features with each other (i.e., conserved), the amino acid at each position of a protein herein can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

The term "isolated" as used herein refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, an isolated polynucleotide or polypeptide molecule can be comprised within a cell or organism in a heterologous manner. Another example is an isolated glucosyltransferase enzyme or reaction. "Isolated" herein can also characterize an aqueous composition herein. As such, an aqueous composition of the present disclosure is synthetic/man-made, and/or has properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

New processes for enzymatic production of fructose syrup (FS) are sought after that require less processing steps and/or additives. To that end, disclosed herein is FS comprising at least 55% fructose on a dry weight basis (dwb) and production methods thereof employing a glucosyltransferase reaction.

Certain embodiments of the present disclosure concern a method for producing an aqueous composition comprising fructose. This method comprises at least:

(a) contacting water, sucrose, and a glucosyltransferase enzyme that synthesizes poly alpha-1,3-glucan having at least 30% alpha-1,3-linkages to produce a soluble fraction and an insoluble fraction, wherein the insoluble fraction comprises the poly alpha-1,3-glucan, and wherein the soluble fraction comprises at least about 55% fructose on a dry weight basis, and (b) separating the soluble fraction from the insoluble fraction, thereby providing an aqueous composition comprising fructose.

Significantly, although one or more chromatographical process can be applied if desired to enhance results, such additional processing is not necessary to reach the 55% fructose (dwb) level. It would be understood that a soluble fraction produced in the glucosyltransferase reaction of this method represents the aqueous composition as directly produced by the method (i.e., the aqueous composition likewise comprises 55% fructose [dwb]). Thus, disclosures herein regarding a soluble fraction can likewise apply to the disclosure of an aqueous composition, unless otherwise noted. Step (a) can optionally be characterized as providing a reaction by virtue of contacting each of the water, sucrose and enzyme components with each other.

A soluble fraction (and therefore an aqueous composition produced by the above method) herein comprises at least about 55% fructose (dwb). For example, there can be at least about 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, or 98% fructose on a dry weight basis in a soluble fraction herein. In other examples, there can be about 55-95%, 55-90%, 55-85%, 55-80%, 55-75%, 55-70%, 60-95%, 60-90%, 60-60%, 60-80%, 60-75%, 60-70%, 65-95%, 65-90%, 65-85%, 65-80%, 65-75%, 65-70%, 70-95%, 70-90%, 70-85%, 70-80%, 70-75%, 75-95%, 75-90%, 75-85%, 75-80%, 80-95%, 80-90%, 80-85%, 85-95%, 85-90%, or 90-95% fructose on a dry weight basis in a soluble fraction. In some embodiments in which a soluble fraction has been subjected at least to an oligosaccharide (e.g., leucrose) hydrolytic procedure (e.g., enzymatic hydrolysis) and/or nanofiltration, there can be at least about 65% fructose on a dry weight basis in the soluble fraction.

A soluble fraction in some aspects can comprise about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 3-24%, 4-24%, 6-24%, 8-24%, 10-24%, 12-24%, 14-24%, 16-24% glucose on a dry weight basis. In some embodiments in which a soluble fraction has been subjected at least to an oligosaccharide (e.g., leucrose) hydrolytic procedure (e.g., enzymatic hydrolysis) and/or nanofiltration, there can be about 14-24%, 14-20%, 14-18%, 14-16%, 15-24%, 15-20%, 15-18%, or 15-16% (dwb) glucose.

A soluble fraction in some aspects can comprise soluble oligosaccharides with a degree of polymerization (DP) of 2 to about 15. The DP of such oligosaccharides can range from 2-7, 2-8, 2-9, 2-10, 2-11, 2-12, 2-13, 2-14, or 2-15, for example. Examples of the oligosaccharides include one or more of sucrose (i.e., residual sucrose that was not converted in the glucosyltransferase reaction), leucrose, trehalulose, isomaltulose, maltulose, isomaltose, nigerose and turanose. All of these oligosaccharides, at least, can be present in a soluble fraction in certain embodiments. The oligosaccharides present can be maltulose, leucrose, trehalulose, isomaltulose, and isomaltose in some aspects. In these and/or certain other embodiments, oligosaccharides of a soluble fraction can comprise glucose and/or fructose. There can be at least about 65%, 70%, 75%, 80%, 85%, 86%, 87%, 88%, 89%, 90%, 91%, 92%, 93%, 94%, or 95 wt % glucose content in the soluble oligosaccharides, for example. In some embodiments, oligosaccharides can include fructan disaccharides (i.e., DP2 oligomers comprising only fructose). The relative amount of trehalulose in a soluble fraction can be about, or at least about, 2, 2.5, 3, 3.5, 4, or 5 times more, for example, than the relative amount of sucrose, maltulose, leucrose, turanose, isomaltulose, and/or isomaltose also present in the soluble fraction. In some aspects, the relative amount of leucrose in a soluble fraction can be nearly the same (e.g., ±5%, 10%, 15%) as the relative amount of isomaltose and/or maltulose. Still in some aspects, the aforementioned relative amounts of disaccharides can characterize a soluble fraction that has been subject to an enzymatic hydrolysis procedure.

A soluble fraction in some aspects can comprise less than about 30% of soluble oligosaccharides on a dry weight basis. For example, there may be less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%, for example, of soluble oligosaccharides on a dry weight basis in the soluble fraction. In some embodiments in which a soluble fraction has been subjected at least to an oligosaccharide (e.g., leucrose) hydrolytic procedure (e.g., enzymatic hydrolysis) and/or nanofiltration, there may be less than about 15%, 14%, 13%, 12%, 11%, 10%, 9%, 8%, 7%, 6% 5%, 4%, 3%, 2% or 1%, for example, of soluble oligosaccharides on a dry weight basis in the soluble fraction. In some aspects of the present disclosure, there is some amount of soluble oligosaccharides present in a soluble fraction (i.e., the level of oligosaccharides is not 0% dwb).

A soluble fraction in some aspects can comprise less than about 20%, 19%, 18%, 17%, 16%, 15%, 14%, 13%, 12%, 11%, 10%, 9%, 8%, 7%, 6%, 5%, 4%, 3%, 2%, or 1% leucrose on a dry weight basis. In some embodiments in which a soluble fraction has been subjected at least to an oligosaccharide (e.g., leucrose) hydrolytic procedure (e.g., enzymatic hydrolysis) and/or nanofiltration, there may be less than about 3%, 2%, or 1% (dwb) leucrose.

A sub-population of the oligosaccharides in a soluble fraction in some aspects (e.g., DP2-7 or DP2-8) can comprise alpha-1,3 glucosidic linkages and/or alpha-1,6 glucosidic linkages. Such a sub-population of oligosaccharides can optionally be said to comprise only glucose (no fructose), whereas in other aspects some oligosaccharides of this sub-population can comprise fructose. Oligosaccharides in certain embodiments of this sub-population can comprise about 60-99% alpha-1,3 glucosidic linkages and about 1-40% alpha-1,6 glucosidic linkages. Such oligosaccharides alternatively can comprise about 60-95% or 70-90% alpha-1,3 glucosidic linkages, and about 5-40% or 10-30% alpha-1,6 glucosidic linkages. Alternatively still, such oligosaccharides herein can comprise about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% alpha-1,3 glucosidic linkages, and about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% alpha-1,6 glucosidic linkages. The aforementioned oligosaccharides can collectively comprise any of the foregoing linkage profiles. By "collectively comprise", it is meant that the total or average linkage profile of a mixture of the oligosaccharides is any of the foregoing linkage profiles. The aforementioned oligosaccharides can contain mostly alpha-1,3 and alpha-1,6 glucosidic linkages. For example, at least 95%, 96%, 97%, 98%, 99%, or 100% of the linkages of the oligosaccharide sub-population are alpha-1,3 and alpha-1,6 glucosidic linkages. Other linkages, if present in the oligosaccharides, may be alpha-1,4 or alpha-1,2 glucosidic linkages, and/or fructose linkages, for example.

In some aspects, a sub-population of oligosaccharides as described above can represent about 32, 33, 34, 35, 36, 37, 38, 39, 40, 41, 42, 43, 44, 45, 32-45, 32-42, 32-39, 35-45, 35-42, 35-39, 38-45, or 38-42 wt % of all the oligosaccharides of a soluble fraction. The percent dry solids basis (dsb) of these oligosaccharides in a soluble fraction can be about 2%, 3%, 4%, 5%, 6%, 7%, 8%, 9%, 10% 2-10%, 4-10%, 6-10%, 2-8%, 4-8%, 6-8%, 2-6%, or 4-6%, for example. These percentages/amounts are typically observed in a soluble fraction herein in which there has been no oligosaccharide (e.g., leucrose) hydrolytic procedure (e.g., enzymatic hydrolysis) and/or nanofiltration. Alternatively, a sub-population of oligosaccharides as described above can represent about 85, 86, 87, 88, 89, 90, 91, 92, 93, 94, 95, 85-95, 87.5-95, 90-95, 85-92.5, 87.5-92.5, 90-92.5, 85-90, or 87.5-90 wt %, for example, of all the oligosaccharides of a soluble fraction that has been treated with an oligosaccharide (e.g., leucrose) hydrolytic procedure (e.g., enzymatic hydrolysis) (but optionally no nanofiltration). The percent dry solids basis (dsb) of these oligosaccharides in a soluble fraction that has been hydrolytically treated can be about 15%, 16%, 17%, 18%, 19%, 20%, 15-20%, 16-19%, or 17-18%, for example.

A soluble fraction can be a portion of (e.g., at least about 70-80%), or all of, the liquid solution from a glucosyltransferase reaction. Typically, a soluble fraction is separated from an insoluble glucan product(s) synthesized in the reaction. For example, a soluble fraction can be separated from one or more glucan products that are insoluble in water (e.g., poly alpha-1,3-glucan) which fall out of solution during their synthesis. A soluble fraction in certain embodiments of the present disclosure is from a poly alpha-1,3-glucan synthesis reaction.

The volume of a soluble fraction (before optionally diluting or concentrating the fraction, see below) in certain embodiments can be at least about 10%, 20%, 30%, 40%, 50%, 60%, 70%, 80% or 90% (or any integer value between 10% and 90%) of the volume of the glucosyltransferase reaction from which it is obtained, for example. A soluble fraction can be obtained at any stage of a glucosyltransferase reaction, but is preferably obtained near (e.g., greater than 80 or 90% complete) or after completion of the reaction.

Examples of a soluble fraction of a glucosyltransferase reaction in certain embodiments include filtrates and supernatants; a filtrate or supernatant can also be considered as an aqueous composition of the present disclosure. Thus, a soluble fraction herein can be obtained (separated) from a glucosyltransferase reaction using a funnel, filter (e.g., a surface filter such as a rotary vacuum-drum filter, cross-flow filter, screen filter, belt filter, screw press, or filter press with or with membrane squeeze capability; or a depth filter such as a sand filter), centrifuge, and/or any other method or equipment known in the art that allows removal of some or all liquids from solids. Any configuration useful for separating soluble and insoluble fraction can be used. Filtration can be by gravity, vacuum, or press filtration, for example. Filtration preferably removes all or most of an insoluble glucan; any filter material (e.g., cloth, metal screen or filter paper) with an average pore size (e.g., ~10-50 micron) sufficient to remove solids from liquids can be used. A soluble fraction typically retains all or most of its dissolved components, such as certain byproducts (e.g., glucose, oligosaccharides such as leucrose) of the glucosyltransferase reaction. Optionally, all or most of any residual amount of soluble fraction remaining with the insoluble fraction following a separation step herein can be obtained by washing the insoluble fraction one or more times with water or an aqueous solution. Such washing can be done one, two, or more times with a wash volume that is at least about 10-100% of the volume of the gtf reaction used to produce the soluble and insoluble fractions, for example. Washing can be done by various modes, such as displacement or reslurry washing. Wash liquid that is separated from the insoluble fraction can be combined with the originally isolated soluble fraction.

A soluble fraction herein can optionally be diluted or concentrated, if desired. Concentration of a soluble fraction can be performed using any method and/or equipment known in the art suitable for concentrating a solution. Concentration of a soluble fraction is preferably performed in such a way as to minimize color production. For example, a fraction can be concentrated by evaporation, such as with a rotary evaporator. Other suitable types of evaporation equipment include forced circulation or falling film evaporators. A preferred evaporator is a falling film evaporator, which in some aspects uses multiple effects or vapor recompression to minimize energy consumption. Concentration is typically done at pressures below atmospheric pressure to minimize color formation. Concentration may be done in multiple stages if desired. For example, a soluble fraction herein can be evaporated to about 30-60 wt % dry solids (DS) at one temperature and pressure, and then evaporated to about 30-80 wt % DS (~30-60 wt % DS, ~70-77 wt % DS) at a lower temperature and pressure (compared to the first stage) to minimize formation of color in the final syrup. A concentrated soluble fraction (e.g., concentrated filtrate) can optionally be referred to as a syrup. Fructose syrup herein can be concentrated to about 65-77 wt % solids to increase shelf life and prevent microbial growth, for example.

A soluble fraction in certain embodiments is from a poly alpha-1,3-glucan synthesis reaction; such a fraction is preferably a filtrate. A fraction of a poly alpha-1,3-glucan synthesis reaction herein can comprise at least water, fructose and one or more other saccharides (e.g., glucose and oligosaccharides such as leucrose), for instance. Other components that may be in this type of soluble fraction include sucrose (i.e., residual sucrose not consumed in the gtf reaction), proteins, ions, and/or organic acids, for example. Minimally, the components of a soluble fraction from a poly alpha-1,3-glucan synthesis reaction include water, fructose, glucose, one or more oligosaccharides (DP2-7 or DP2-8, including leucrose, for example), and optionally sucrose, for example. It would be understood that the composition of a soluble fraction depends, in part, on the conditions of the glucosyltransferase reaction from which the fraction is obtained.

In certain embodiments, a soluble fraction herein does not contain any borates (e.g., boric acid, tetraborate), or contains less than 50, 100, 150, 200, 250, or 300 mM of a borate. It would be understood that, in cases in which a soluble fraction of a reaction herein is intended for use as an ingestible product such as a food or pharmaceutical product, borate is not present or is otherwise undetectable in the soluble fraction.

It should be understood that the exact distribution of sugar byproducts produced in a glucosyltransferase reaction can vary based on the reaction conditions and gtf enzyme used, especially on temperature and sucrose concentration. Generally, as the amount of sucrose is increased, the selectivity of the reaction towards both leucrose and oligosaccharides will increase. Conversely, as the temperature increases, the selectivity of the reaction towards leucrose tends to decrease, while the selectivity towards oligosaccharides is largely unaffected. It should also be understood that the ratio of sugars to water, i.e., wt % DS, which is calculated by dividing the mass of sugar to total solution weight, can be adjusted either by evaporation or addition of water without a significant impact to the relative distribution of sugars in the soluble fraction. It is also possible to increase the percentage of sucrose in a fraction by stopping the gtf reaction before complete conversion (to glucan) is achieved, either by reducing the pH below the active range for the gtf enzyme or by thermal deactivation of the gtf enzyme.

An insoluble fraction is produced in the glucosyltransferase reaction of the disclosed method that comprises poly alpha-1,3-glucan. It would therefore be understood that such glucan polymer is aqueous-insoluble under the conditions of a glucosyltransferase reaction herein (e.g., pH 4-9), which are non-caustic. Poly alpha-1,3-glucan herein comprises at least 30% alpha-1,3-glucosidic linkages.

Poly alpha-1,3-glucan in certain embodiments has at least about 95%, 96%, 97%, 98%, 99%, or 100% alpha-1,3 glucosidic linkages. In some embodiments, accordingly, poly alpha-1,3-glucan has less than about 5%, 4%, 3%, 2%, 0 or 0% of glucosidic linkages that are not alpha-1,3. It should be understood that the higher the percentage of alpha-1,3-glucosidic linkages present in poly alpha-1,3-glucan, the greater the probability that the poly alpha-1,3-glucan is linear, since there are lower occurrences of certain linkages forming branch points in the polymer. Thus, poly alpha-1,3-glucan with 100% alpha-1,3 glucosidic linkages is believed to be completely linear. In certain embodiments, poly alpha-1,3-glucan has no branch points or less than about 5%, 4%, 3%, 2%, or 1% branch points as a percent of the glycosidic linkages in the polymer. Examples of branch points include alpha-1,6 branch points.

Poly alpha-1,3-glucan (≥95% 1,3 linkages) herein can have a molecular weight in $DP_w$ or $DP_n$ of at least about 100 in some aspects. For example, the molecular weight can be at least about 400 $DP_w$ or $DP_n$. $DP_w$ or $DP_n$ in still another embodiment can be at least about 100, 150, 200, 250, 300, 350, 400, 450, 500, 550, 600, 650, 700, 750, 800, 850, 900, 950, 1000, 1100, 1200, 1300, 1400, or 1500 (or any integer between 100 and 1500).

Poly alpha-1,3-glucan (≥95% 1,3 linkages) is insoluble in most aqueous systems. In general, the solubility of a glucan polymer in an aqueous systems is related to its linkage type, molecular weight and/or degree of branching. Poly alpha-1,3-glucan (≥95% 1,3 linkages) is generally insoluble at a $DP_w$ of 8 and above in aqueous (or mostly aqueous) liquids at 20° C.

In some other embodiments, an insoluble poly alpha-1,3-glucan can comprise at least 30% alpha-1,3-glucosidic linkages and a percentage of alpha-1,6-glucosidic linkages that brings the total of both the alpha-1,3 and -1,6 linkages in the poly alpha-1,3-glucan to 100%. For example, the percentage of alpha-1,3 linkages can be at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, while the percentage of alpha-1,6 linkages can be that which brings the total of both the alpha-1,3 and -1,6 linkages in the in the poly alpha-1,3-glucan to 100%. Poly alpha-1,3-glucan in these embodiments does not comprise alternan (alternating 1,3 and 1,6 linkages).

Step (a) of a method herein of producing an aqueous composition comprising fructose includes forming a glucosyltransferase reaction. Such an enzymatic reaction employs a glucosyltransferase that synthesizes poly alpha-1,3-glucan comprising at least about 30% alpha-1,3-glucosidic linkages. A glucosyltransferase enzyme herein can produce any aqueous-insoluble poly alpha-1,3-glucan molecule as disclosed above, such as one comprising at least 95% alpha-1,3-glucosidic linkages.

A glucosyltransferase enzyme in certain embodiments for producing poly alpha-1,3-glucan (≥95% 1,3 linkages) can comprise, or consist of, an amino acid sequence that is at least 90%, 91%, 92%, 93%, 94%, 95%, 96%, 97%, 98%, 98.5%, 99%, or 99.5% identical to SEQ ID NOs:1, 2, 3, 4, or 5. Further, this glucosyltransferase can produce (along with poly alpha-1,3-glucan as an insoluble product) soluble products comprising at least 55% fructose on a dry weight basis of the soluble products. A glucosyltransferase in some aspects produces soluble products comprising about, or at least about, any of the fructose amounts disclosed above (e.g., at least 65% or 80% dwb).

A glucosyltransferase enzyme in certain embodiments can comprise, or consist of, a glucosyltransferase catalytic domain having an amino acid sequence that is at least 90%, 91%, 92%, 93%, 94%, 95%, 96%, 97%, 98%, 98.5%, 99%, or 99.5% identical to amino acid positions 54-957 of SEQ ID NO:1, and can produce soluble products comprising at least 55% fructose on a dry weight basis (or any higher amount as disclosed above) of the soluble products. A glucosyltransferase enzyme with amino acid positions 54-957 of SEQ ID NO:1 can produce poly alpha-1,3-glucan with 100% alpha-1,3 linkages and a DPw of at least 400 (data not shown, refer to Table 6 of U.S. Pat. Appl. No. 62/180,779), for example.

SEQ ID NOs:1 (GTF 7527), 2 (GTF 2678), 3 (GTF 6855), 4 (GTF 2919), and 5 (GTF 2765) each represent a glucosyltransferase that, compared to its respective wild type counterpart, lacks the signal peptide domain and all or a substantial portion of the variable domain. Thus, each of these glucosyltransferase enzymes has a catalytic domain followed by a glucan-binding domain. The approximate location of catalytic domain sequences in these enzymes is as follows: 7527 (residues 54-957 of SEQ ID NO:1), 2678 (residues 55-960 of SEQ ID NO:2), 6855 (residues 55-960 of SEQ ID NO:3), 2919 (residues 55-960 of SEQ ID NO:4), 2765 (residues 55-960 of SEQ ID NO:5). The amino acid sequences of catalytic domains of GTFs 2678, 6855, 2919 and 2765 have about 94.9%, 99.0%, 95.5% and 96.4% identity, respectively, with a catalytic domain sequence of GTF 7527 (i.e., amino acids 54-957 of SEQ ID NO:1). These particular glucosyltransferase enzymes can produce poly alpha-1,3-glucan with 100% alpha-1,3 linkages and a DPw of at least 400 (data not shown, refer to Table 4 of U.S. Pat. Appl. No. 62/180,779). Thus, a glucosyltransferase enzyme in certain embodiments can (i) comprise, or consist of, a glucosyltransferase catalytic domain that is at least 90%, 91%, 92%, 93%, 94%, 95%, 96%, 97%, 98%, 98.5%, 99%, or 99.5% identical to the amino acid sequence of a catalytic domain of GTF 2678, 6855, 2919, or 2765, and (ii)

produce soluble products comprising at least 55% fructose on a dry weight basis (or any higher amount as disclosed above) of the soluble products. In some alternative embodiments, a glucosyltransferase catalytic domain sequence does not comprise residues 54-957 of SEQ ID NO:1, residues 55-960 of SEQ ID NO:2, residues 55-960 of SEQ ID NO:3, residues 55-960 of SEQ ID NO:4, or residues 55-960 of SEQ ID NO:5.

Although it is believed that a glucosyltransferase enzyme herein need only have a catalytic domain sequence, such as one comprising an amino acid sequence that is at least 90% identical to amino acid positions 54-957 of SEQ ID NO:1 (or positions 55-960 of SEQ ID NO:2, positions 55-960 of SEQ ID NO:3, positions 55-960 of SEQ ID NO:4, or positions 55-960 of SEQ ID NO:5), the glucosyltransferase enzyme can be comprised within a larger amino acid sequence. For example, the catalytic domain may be linked at its C-terminus to a glucan-binding domain, and/or linked at its N-terminus to a variable domain and/or signal peptide.

Still further examples of glucosyltransferase enzymes can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A glucosyltransferase enzyme herein typically lacks an N-terminal signal peptide.

The amino acid sequence of a glucosyltransferase enzyme in certain aspects has been modified such that the enzyme produces more products (poly alpha-1,3-glucan and fructose), and less byproducts (e.g., glucose, oligosaccharides such as leucrose), from a given amount of sucrose substrate. For example, one, two, three, or more amino acid residues of the catalytic domain of a glucosyltransferase herein can be modified to obtain an enzyme that produces at least about 55% fructose (or any higher amount as disclosed above) on a dry weight basis of the soluble products of the enzyme.

A glucosyltransferase enzyme herein can be derived from any microbial source, such as a bacteria or fungus. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A glucosyltransferase enzyme herein can be prepared by fermentation of an appropriately engineered microbial strain, for example. Recombinant enzyme production by fermentation is well known in the art using microbial strains such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*) and *Trichoderma* (e.g., *T. reesei*) (e.g., see Adrio and Demain, *Biomolecules* 4:117-139, which is incorporated herein by reference). A nucleotide sequence encoding a glucosyltransferase enzyme amino acid sequence is typically linked to a heterologous promoter sequence to create an expression cassette for the enzyme. Such an expression cassette may be incorporated on a suitable plasmid or integrated into the microbial host chromosome, using methods well known in the art. The expression cassette may include a transcriptional terminator nucleotide sequence following the amino acid coding sequence. The expression cassette may also include, between the promoter sequence and amino acid coding sequence, a nucleotide sequence encoding a signal peptide that is designed to direct secretion of the glucosyltransferase enzyme. At the end of fermentation, cells may be ruptured accordingly and the glucosyltransferase enzyme can be isolated using methods such as precipitation, filtration, and/or concentration. Alternatively, a lysate comprising a glucosyltransferase can be used without further isolation. The activity of a glucosyltransferase enzyme can be confirmed by biochemical assay, such as measuring its conversion of sucrose to glucan polymer.

A glucosyltransferase enzyme in certain embodiments does not occur in nature. For example, an enzyme herein is not believed to be one that is naturally secreted (i.e., mature form) from a microbe (from which the glucosyltransferase enzyme herein could possibly have been derived).

The temperature of a glucosyltransferase reaction herein can be controlled, if desired. In certain embodiments, the temperature of the reaction can be between about 5° C. to about 50° C. The temperature in certain other embodiments can be between about 20° C. to about 40° C., or about 20° C. to about 30° C. (e.g., about 22-25° C.).

The initial concentration of sucrose in a reaction solution herein can be about 20 g/L to about 400 g/L, for example. Alternatively, the initial concentration of sucrose can be about 75 g/L to about 175 g/L, or from about 50 g/L to about 150 g/L. Alternatively still, the initial concentration of sucrose can be about 40, 50, 60, 70, 80, 90, 100, 110, 120, 130, 140, 150, or 160 g/L (or any integer value between 40 and 160 g/L), for example. "Initial concentration of sucrose" refers to the sucrose concentration in a glucosyltransferase reaction just after all the reaction components have been added (e.g., at least water, sucrose, glucosyltransferase enzyme).

Sucrose used in a glucosyltransferase reaction herein can be highly pure (≥99.5%) or be of any other purity or grade. For example, sucrose can have a purity of at least 99.0%, or can be reagent grade sucrose.

The pH of a glucosyltransferase reaction in certain embodiments can be between about 4.0 to about 8.0, or between about 5.0 to about 6.0. Alternatively, the pH can be about 4.0, 4.5, 5.0, 5.5, 6.0, 6.5, 7.0, 7.5, or 8.0, for example. The pH can be adjusted or controlled by the addition or incorporation of a suitable buffer, including but not limited to: phosphate, tris, citrate, or a combination thereof. Buffer concentration in a glucan synthesis reaction can be from 0 mM to about 100 mM, or about 10, 20, or 50 mM, for example. A glucan synthesis reaction in some preferred aspects uses a minimal amount of buffer, such as about 10 mM or less.

One or more different glucosyltransferase enzymes may be used in certain aspects. A glucosyltransferase reaction herein may contain one, two, or more glucosyltransferase enzymes, for example.

A method as presently disclosed for producing an aqueous composition with fructose comprises providing a reaction by contacting at least water, sucrose, and a glucosyltransferase enzyme as described herein. These and optionally other reagents can be added altogether or added in any order. It will be understood that as the glucosyltransferase enzyme synthesizes poly alpha-1,3-glucan, the reaction, which initially is in the form of a solution, becomes a mixture since insoluble poly alpha-1,3-glucan falls out of solution. The contacting step of the disclosed method can be performed in any number of ways. For example, the desired amount of sucrose can first be dissolved in water (optionally, other components may also be added at this stage of preparation, such as buffer components), followed by the addition of at least one glucosyltransferase enzyme. The solution may be kept still, or agitated via stirring or orbital shaking, for example. Typically, a glucan synthesis reaction is cell-free.

Additional components of a glucosyltransferase reaction can be any of those as disclosed above and/or in the instant Examples. In some instances, no borate (e.g., boric acid, tetraborate) or less than 50, 100, 150, 200, 250, or 300 mM of a borate is used in a reaction. A borate may optionally be present and/or be above any of the foregoing concentrations, in a glucosyltransferase reaction that (i) otherwise has the capability to yield, without borate addition, a soluble fraction with at least about 65%, 70%, or 75% fructose on a dry weight basis, and (ii) is not used for preparing an ingestible product. It would be understood that, in cases in which a soluble fraction of a reaction herein is intended for use as an ingestible product such as a food or pharmaceutical product, borate is not present or is otherwise undetectable in the soluble fraction. In some instances, a glucosyltransferase reaction comprises, or does not comprise, a semi-permeable membrane (e.g., molecular weight cut-off from 12,000 to 100,000 Daltons).

Completion of a reaction in certain embodiments can be determined visually (no more accumulation of insoluble poly alpha-1,3-glucan) and/or by measuring the amount of sucrose left in the solution (residual sucrose), where a percent sucrose consumption of over about 90% can indicate reaction completion, for example. Typically, a reaction of the disclosed process will take about 12, 24, 36, 48, 60, 72, 84, or 96 hours to complete, depending on certain parameters such as the amount of sucrose and glucosyltransferase enzyme used in the reaction, and/or the temperature of the reaction.

The percent sucrose consumption of a glucosyltransferase reaction in certain embodiments is at least about 90%, 91%, 92%, 93%, 94%, 95%, 96%, 97%, 98%, 99%, or 100% of the sucrose initially contacted with water and a glucosyltransferase enzyme. Alternatively, the percent sucrose consumption may be >95% or >99%.

The yield of poly alpha-1,3-glucan produced in some aspects of a glucosyltransferase reaction herein can be at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% based on the weight of sucrose converted in the reaction.

The yield of fructose produced in some aspects of a glucosyltransferase reaction herein is at least about 35%, 36%, 37%, 38%, 39%, 40%, 41%, 42%, 43%, 44%, 45%, 46%, 47%, 48%, 49%, or 50% based on the weight of sucrose converted in the reaction. or 50% based on the weight of sucrose converted in the reaction.

Poly alpha-1,3-glucan produced in a glucosyltransferase reaction of the instantly disclosed method can be isolated. Such isolation can be characterized to represent the method step herein of separating the soluble fraction from the insoluble fraction, thereby providing an aqueous composition comprising fructose.

A method of producing an aqueous composition comprising fructose in certain aspects of the instant disclosure can further comprise contacting a soluble fraction and/or a glucosyltransferase reaction with an alpha-glucosidase enzyme to hydrolyze at least one glycosidic linkage of one or more oligosaccharides present in the soluble fraction and/or glucosyltransferase reaction, thereby increasing the monosaccharide content in the soluble fraction. Thus, a soluble fraction herein can be contacted with an alpha-glucosidase after its separation from an insoluble fraction comprising poly alpha-1,3-glucan, or before its separation (e.g., while it is being formed in the reaction, and/or after completion of the reaction) (i.e., in contacting step [a] and/or after separation step [b]). The activity of an alpha-glucosidase hydrolyzes one or more different oligosaccharides herein (e.g., leucrose and/or oligosaccharides comprising only glucose) to its constituent monosaccharides (fructose and/or glucose). Embodiments herein comprising alpha-glucosidase treatment can optionally be characterized as further comprising an enzymatic hydrolysis step. Where treatment is with an alpha-glucosidase that hydrolyzes a fructose-comprising oligosaccharide such as leucrose, such treatment will increase the fructose content (dwb) of the soluble fraction.

An alpha-glucosidase herein, and methods of its use in a soluble fraction and/or glucosyltransferase reaction, can be as disclosed in U.S. Patent Appl. Publ. Nos. 2015/0240278 and 2015/0240279, which are incorporated herein by reference. An alpha-glucosidase (EC 3.2.1.20) can be used in certain embodiments herein to hydrolyze an alpha-1,5 glucosyl-fructose linkage in a saccharide comprising at least one alpha-1,5 glucosyl-fructose linkage (e.g., leucrose). A transglucosidase (EC 2.4.1.24; 1,4-alpha-glucan 6-alpha-glucosyltransferase) or glucoamylase (EC 3.2.1.3; alpha-1,4-glucan glucohydrolase) can be used, for example, as an alpha-glucosidase to hydrolyze an alpha-1,5 glucosyl-fructose linkage in a saccharide comprising at least one alpha-1,5 glucosyl-fructose linkage (e.g., leucrose). Examples of suitable alpha-glucosidases (disclosed in U.S. Appl. Publ. Nos. 2015/0240278 and 2015/0240279) include the mature forms of "TG L-2000" (*Aspergillus niger transglucosidase*), "GC 321 Glucoamylase" (*Trichoderma reesei glucoamylase*, TrGA), "AcIglu1" (*Aspergillus clavatus* alpha-glucosidase), "AcIglu1" (*Aspergillus clavatus* alpha-glucosidase), "Nfiglu1" (*Neosartorya fischeri* alpha-glucosidase), "Nfiglu1" (*Neosartorya fischeri* alpha-glucosidase), "Ncrglu1" (*Neurospora crassa* alpha-glucosidase), "Ncrglu1" (*Neurospora crassa* alpha-glucosidase), "TauSec098" (*Rasamsonia composticola* alpha-glucosidase), "TauSec098" (*Rasamsonia composticola* alpha-glucosidase), "TauSec099" (*Rasamsonia composticola* alpha-glucosidase), "TauSec099" (*Rasamsonia composticola* alpha-glucosidase), "BloGlu1" (*Bifidobacterium longum* (subsp. *longum* JDM301) alpha-glucosidase), "BloGlu2" (*Bifidobacterium longum* alpha-glucosidase), "BloGlu3" (*Bifidobacterium longum* (subsp. F8) alpha-glucosidase), "BpsGlu1" (*Bifidobacterium pseudolongum* alpha-glucosidase), "BthGlu1" (*Bifidobacterium thermophilum* RBL67 alpha-glucosidase), "BbrGlu2" (*Bifidobacterium breve* alpha-glucosidase), and "BbrGlu5" (*Bifidobacterium breve* ACS-071-V-Sch8b alpha-glucosidase), or any amino acid sequence that (i) is at least about 90%, 91%, 92%, 93%, 94%, 95%, 96%, 97%, 98%, or 99% identical to any of these enzymes and (ii) has hydrolytic activity toward alpha-1,5 glucosyl-fructose linkages in saccharides. One or more of alpha-glucosidase enzymes herein may be used in a hydrolysis reaction in certain embodiments. Both a transglucosidase and glucoamylase can be used in a reaction, for example.

Typically, a soluble fraction and/or a glucosyltransferase reaction herein can be contacted directly, without modification, with one or more alpha-glucosidases. The following conditions, however, may be useful for performing enzymatic hydrolysis. The pH can be about 3.0 to 9.0 (e.g., 4.0-5.0), for example. The temperature can be about 20° C. to about 80° C. (e.g., 55-65° C., or 60° C.), for example. Enzymatic hydrolysis can be performed for a period of at least about 10 minutes to about 90 hours, for example. In certain embodiments, such as for hydrolyzing leucrose, a hydrolysis reaction can be performed in less than 4 hours (e.g., 0.5-4 hours). The duration of the hydrolysis reaction is typically impacted by the amount of enzyme added and the amount of oligosaccharides to be hydrolyzed. A soluble fraction that has been concentrated down to a syrup can be used in a hydrolysis reaction in some aspects. One or more gtf enzymes present in a soluble fraction of glucosyltransferase reaction can optionally be deactivated (e.g., heat-deactivated) before use thereof in an enzymatic hydrolysis. The hydrolysis enzymes present in the hydrolyzed fraction are typically destroyed using thermal denaturation after the completion of hydrolysis.

An alpha-glucosidase in certain embodiments may be immobilized. The enzyme may be immobilized using any method and/or means known in the art, such as those disclosed in U.S. Pat. Nos. 5,541,097 and 4,713,333, which are incorporated herein by reference. For example, one or more enzymes can be immobilized by contacting the enzyme(s) with a solution of an amine-reactive material (e.g., glutaraldehyde) to form an adduct (e.g., enzyme-glutaraldehyde adduct), after which the adduct is bonded to a solid carrier that has been treated with a polyamine (e.g., a polyethylenimine such as EPOMIN P-1050). A solid carrier (solid support) to which an alpha-glucosidase enzyme can be immobilized in certain embodiments can be an inorganic or organic material. Such materials include, for example, gamma-alumina, titania, activated granular carbon, granular diatomaceous earth, glass beads, porous glass, pumice-stone, silica gel, metal oxide and aluminum oxide.

An increase of the monosaccharide content (dwb) (e.g., fructose plus glucose) in a soluble fraction resulting from alpha-glucosidase treatment herein can be about, or at least about, 5%, 10%, 20%, 30%, 40%, 50%, 60%, 70%, 80%, 90%, 100%, 50-80%, 50-90%, 60-80%, or 60-90% as compared to the monosaccharide content in the soluble fraction as it existed before alpha-glucosidase treatment (separated or not separated from ongoing or completed glucosyltransferase reaction). An increase of the fructose content (dwb) in a soluble fraction resulting from alpha-glucosidase treatment can be by about, at least about, or no more than about, 3%, 4%, 5%, 6%, 7%, 8%, 9%, 10%, 11%, 12%, 13%, 14%, 15%, 20%, 30%, 40%, 50%, 10-40%, 10-50%, 20-40%, or 20-50%, for example, as compared to the fructose content in the soluble fraction as it existed before alpha-glucosidase treatment (separated or not separated from ongoing or completed glucosyltransferase reaction).

A method of producing an aqueous composition comprising fructose in certain aspects can further comprise a process step that increases the content of monosaccharides (e.g., dwb) relative to the content of other saccharides (e.g., oligosaccharides) in a soluble fraction. Such a process step can be in addition to, or instead of, performing an enzymatic hydrolysis step as disclosed above, for example. Also, such a process step is typically performed after separating insoluble poly alpha-1,3-glucan from a soluble fraction of a glucosyltransferase reaction.

A process comprising nanofiltration can be used in some aspects of the present disclosure, and is generally suitable for increasing the monosaccharide content by removing oligosaccharides from a soluble fraction. Nanofiltration typically realizes separations on the basis of size: smaller molecules such as fructose and glucose can pass through a membrane, and larger molecules such as oligosaccharides cannot pass through the membrane. Several structural factors, including surface chemistry, porosity, and geometric configuration, can impact the performance of a nanofiltration membrane. Nanofiltration membranes in some aspects can be flat sheets or spiral-wound; the latter membrane type is preferred as it achieves a higher surface area to volume ratio in a skid. The operating conditions of the membrane can also impact nanofiltration performance. Temperature, pH, trans-membrane pressure, and the viscosity and concentration of retentate and permeate can impact membrane performance. Higher temperatures, pH, and transmembrane pressures are preferred. The exact configuration of a nanofiltration unit herein, including the membrane and operating conditions, is not critical to the present disclosure. A commercial nanofiltration setup can optionally be used, comprising either a single stage or multiple stages. A multi-stage nanofiltration system herein is typically operated by recirculating material in a given stage around the membrane and sending a slip stream of the retentate to subsequent stages. A preferred option minimizes the amount of membrane area necessary to achieve a given purification and may use multiple stages. To achieve high yields, diafiltration water can be used to dilute the retentate to maintain a lower viscosity, and may be added to some or all stages of the process. A preferred nanofiltration operation uses less diafiltration water. Nanofiltration membranes herein are typically characterized on the basis of their flux of permeate through the membrane. Preferred membranes have a high flux of desired compounds, such as fructose and glucose. Another consideration for a nanofiltration membrane is that it sufficiently rejects unwanted materials, such as oligosaccharides, protein, and/or salts. Preferred membranes have a high rejection of unwanted materials. Several commercially available nanofiltration membranes, including OSMONICS DESAL 5 DL and OSMONICS DK produced by General Electric (New York, United State); TS40, XN45, P4 and UA60 produced by Trisep Corporation (Galeta, Calif.); NF 245 produced by Dow (Midland, Mich.); or NFX and NFW produced by Synder (Vacaville, Calif.), and other similar membranes are suitable for use herein.

Nanofiltration in certain embodiments can be performed on a soluble fraction that comprises about, or at least about, 20, 25, 30, 35, 40, 45, 50, 55, 60, 30-50, 30-45, 30-40, 35-50, 35-45, 35-40 wt % dry solids. The pH of a soluble fraction to be entered into a nanofiltration process herein can be about 4.0, 4.25, 4.5, 4.75, 5.0, 5.25., 5.5, 5.75, 6.0, 4.0-6.0, 4.0-5.5, 4.0-5.0, 4.0-4.75, 4.0-4.5, 4.25-5.0, 4.25-4.75, or 4.25-4.5. Nanofiltration can be performed, if desired, by continuously recirculating the sample being filtered. About 0.1, 0.5, 1.0, 1.25, 1.5, 1.75, 2.0, 0.1-2.0, 0.1-1.5, 1.25-2.0, 1.25-1.75, 1.25-1.5, 1.5-2.0, or 1.5-1.75 parts diafiltration water can be added per 1 part dry solids of the sample being filtered, for example.

An increase of the monosaccharide content (dwb) (e.g., fructose plus glucose) in a soluble fraction resulting from a process herein such as nanofiltration can be by about, or at least about, 5%, 10%, 15%, 20%, 25%, 30%, 10-30%, 10-25%, 10-20%, 10-15%, 15-30%, 15-25%, or 15-20% as compared to the monosaccharide content in the soluble fraction as it existed before conducting such process. An increase of the fructose content (dwb) in any of these embodiments can be by about, or at least about, 5%, 10%, 15%, 20%, 25%, 30%, 10-30%, 10-25%, 10-20%, 10-15%, 15-30%, 15-25%, or 15-20% as compared to the fructose content in the soluble fraction as it existed before conducting such process. A decrease in the oligosaccharide content (dwb) of a soluble fraction in any of these embodiments can be by about, or at least about, 40%, 50%, 60%, 70%, 80%, 85%, 90%, 95%, 70-95%, 70-90%, 80-95%, 80-90%, 85-95%, 85-90%, or 90-95%.

A soluble fraction that has been treated by nanofiltration (and also enzymatic hydrolysis in some aspects) can have, for example, (i) an ICUMSA value (measured as disclosed herein) of about 700-900, 800-900, or below about 900, and/or (ii) a conductivity of about 3200, 3000-3400, 3000-3300, 3100-3400, 3100-3300, or 3200 µS/cm or below about 3300 µS/cm. Such a soluble fraction can have about 10-30, 15-30, 20-30, 10-25, or 15-25 wt % dry solids, for example.

Other processes besides, or in addition to, nanofiltration that can optionally be used herein to increase the content of monosaccharides relative to the content of other saccharides (e.g., oligosaccharides) in a soluble fraction include, for example, crystallization (e.g., see U.S. Pat. No. 4,634,472) and chromatography such as size-exclusion chromatography, ligand chromatography (ligand conversion or ligand-exchange chromatography such as that based on differential binding to calcium ions), partition chromatography, or anion exchange chromatography.

In some embodiments of the present disclosure, a method of producing an aqueous composition comprising fructose does not comprise a process step that increases the content of fructose relative to the content of other saccharides (e.g., oligosaccharides and/or glucose) in a soluble fraction. For instance, a method in some cases does not comprise crystallization (e.g., see U.S. Pat. No. 4,634,472) and/or chromatography such as size-exclusion chromatography, ligand chromatography (ligand conversion or ligand-exchange chromatography), partition chromatography, or anion-exchange chromatography. In some embodiments, there is no chromatographic process for particularly removing glucose, such as ligand chromatography (e.g., ligand-exchange based on differential binding to calcium ions). Any of these embodiments may, however, optionally comprise a nanofiltration and/or hydrolysis process as disclosed.

A method of producing an aqueous composition comprising fructose in some embodiments can further comprise a polishing step in which ions and/or color are removed from a soluble fraction herein. Such polishing can be performed immediately following preparation of an insoluble fraction from a glucosyltransferase reaction, and/or after its treatment to one or more of the above-disclosed processes (e.g., hydrolysis alone, nanofiltration alone, hydrolysis and nanofiltration). The dry solids content of an aqueous composition herein can optionally be adjusted before polishing; preferred dry solids contents may be 30-70 wt % DS.

Polishing can be achieved, for example, using ion exchange chromatography (typically for ion removal) and/or carbon treatment (typically for color removal) in some certain aspects. For example, a polishing process can employ a series of columns containing either strong acid cation (SAC) ion exchange resin (e.g., IMAC C16 P), weak base anion (WBA) ion exchange resin (e.g., AMBERLITE IRA 92, Dow, Midland, Mich.), strong base anion (SBA) ion exchange resin (e.g. DOWEX 22), and/or activated carbon (AC) (CHEMVIRON CPG, Calgon Carbon Corporation). The columns can contain one or more of these resins, including combinations of strong acid cation exchange resin and one of either weak base anion or strong base anion resins in the same configuration. Such a mixture is referred to in the art as a mixed bed resin. An aqueous composition herein may contact the ion exchange units one or multiple times in one or multiple passes. A preferred configuration removes both cations and anions, including organic acids, from the aqueous composition. Such columns can be configured in series such as SAC→NBA→SAC→NBA→AC. The exact configuration of columns, choice of cation and/or anion exchange resins, and choice of AC are not critical to the present disclosure, and other configurations of columns are feasible herein, including configurations that may use strong base anion ion exchange resins or mixed bed resins. Numerous commercially available ion exchange resins, such as those sold by Dow, Purolite, or others are also suitable. Use of monodisperse particles may be advantageous for reduced fouling in some aspects. Other parameters, such as contact time and temperature, may be adjusted to achieve target specifications. Typical operating conditions for ion exchange resins herein are 2-6 bed volumes (BV) per hour at concentrations from 10-80 wt % (e.g., ~50 wt %) dry solids (DS), where a bed volume is defined as the total volume of settled resin in a column, which includes both the resin and the interstitial space. The temperature can be about 20° C. to about 80° C. (e.g., 55-65° C., or 60° C.), for example. Faster flow rates, lower temperatures, and lower concentrations may be advantageous to reduce epimerization of fructose to glucose, or production of disaccharides. Once an ion exchange resin is partially or completely saturated, the ability of the resin to remove further ions is diminished. The column may then be regenerated through the use of either acid or base, and consequently reused. Activated carbon columns may be regenerated but are more typically disposed or sent back to the vendor for purification. Regeneration procedures for these adsorbents are well known by those of ordinary skill in the art.

The amount of ions and/or color removed from a soluble fraction by applying a polishing treatment herein can be gauged, for example, by monitoring conductivity and/or ICUMSA, respectively, of the soluble fraction resulting from polishing. In some aspects, a soluble fraction that has been polished can have (i) an ICUMSA value (measured as disclosed herein) of about 1-25 or 1-20, or less than 25 or 20, and/or (ii) a conductivity of about 2.5-25, 2.5-20, 2.5-15, 5-25, 5-20, 5-15, 7.5-25, 7.5-20, or 7.5-15 µS/cm, or less than about 25 or 20 µS/cm. Such a soluble fraction can have about 5-15 wt % (e.g., ~10 wt %) dry solids, for example. In some aspects, a soluble fraction herein comprising about 20-40 wt % dry solids (e.g., ~30 wt % DS) can have (i) an ICUMSA value (measured as disclosed herein) of about 30-60, or less than about 50 or 40, and/or (ii) a conductivity less than about 50, 40, or 30 µS/cm. Conductivity herein can be measured at any temperature between about 20-80° C. or 50-70° C. (e.g., ~60° C.), and/or a pH of about 3, 4, 5, 6, 7, 8, or 9, for example. Such a soluble fraction herein can constitute an ingestible product in some embodiments.

An aqueous composition produced by any process disclosed herein, or a related process, is yet another aspect of the present disclosure. Any soluble fraction as presently disclosed can constitute such an aqueous composition, for example. Alternatively, an aqueous composition optionally can replicate a soluble fraction as now presently disclosed, but be produced in a different manner (e.g., components of a soluble fraction as presently disclosed can be brought together, such as in providing a formulation). The following embodiments represent examples of an aqueous composition.

An aqueous composition in some aspects can comprise: (i) at least about 55% fructose on a dry weight basis, (ii) about 3% to about 24% glucose on a dry weight basis, and (iii) soluble oligosaccharides with a degree of polymerization (DP) of 2 to about 15, wherein said oligosaccharides comprise glucose and/or fructose. Certain embodiments of such an aqueous composition can comprise any other fructose content disclosed herein for a soluble fraction, such as at least about 75% fructose on a dry weight basis. Still additional embodiments can comprise any fructose, glucose and/or soluble oligosaccharide (DP2-15) content disclosed herein for a soluble fraction.

Soluble oligosaccharides of an aqueous composition can be, for example, selected from the group consisting of sucrose, leucrose, trehalulose, isomaltulose, maltulose, isomaltose, and nigerose. Soluble oligosaccharides in some embodiments can comprise (i) at least about 90 wt % glucose, and (ii) about 60-99% alpha-1,3 and about 1-40% alpha-1,6 glucosidic linkages. An aqueous composition can comprise less than about 30% of soluble oligosaccharides on a dry weight basis in some aspects. An aqueous composition in some embodiments can (i) be comprised within, or be, an ingestible product, and/or (ii) have a conductivity less than about 50 μS/cm at 30% dry solids and an ICUMSA value less than about 50. In other aspects, an aqueous composition can have any conductivity level and/or ICUMSA level as disclosed elsewhere herein. An aqueous composition in still further aspects can be comprised within, or be, an ingestible product, regardless of its conductivity and/or ICUMSA levels.

An aqueous composition herein can be comprised within, or be, a consumer product such as an ingestible product or non-ingestible product. Examples of an ingestible product are foods/beverages and pharmaceutical products. Examples of non-ingestible products include cosmetics. In certain aspects, an aqueous composition herein can be used as a partial or complete substitute for high fructose corn syrup (HFCS) in a consumer product that typically incorporate HFCS. An aqueous composition herein can be used as a sweetener and/or preservative in an ingestible product or consumer product, for example.

An aqueous composition herein can be utilized in a food, beverage, animal feed, an animal health and nutrition product, pharmaceutical product, and/or cosmetic product, for example. The intended use of an aqueous composition herein in foods and feeds can be to soften texture, add volume, thicken, prevent crystallization of sugar, and/or enhance flavor or sweetness, for example.

Further examples of using an aqueous composition of the present disclosure include its use as: a bulking, binding and/or coating ingredient; a carrier for coloring agents, flavors/fragrances, and/or high intensity sweeteners; a spray drying adjunct; a bulking, bodying and/or dispersing agent; and an ingredient for promoting moisture retention (humectant). Illustrative examples of products that can be prepared using an aqueous composition disclosed herein include food products, beverage products, pharmaceutical products, nutritional products, sports products and cosmetic products. Particular examples of beverage products that can comprise an aqueous composition herein include beverage products such as concentrated beverage mixes, carbonated beverages, non-carbonated beverages, fruit-flavored beverages, fruit juices, teas, coffee, milk nectars, powdered soft drinks, liquid concentrates, milk drinks, smoothies, alcoholic beverages, flavored waters and combinations thereof. Particular examples of food products that can comprise an aqueous composition herein include baked goods (e.g., breads), confectioneries, frozen dairy products, meats, cereal products (e.g., breakfast cereals), dairy products (e.g., yogurt), condiments, snack bars, soups, dressings, mixes, prepared foods, baby foods, diet preparations, peanut butter, syrups, sweeteners, food coatings, pet food, animal feed, animal health and nutrition products, dried fruit, sauces, gravies, jams/jellies, dessert products, spreads, batters, breadings, spice mixes, frostings and the like.

An aqueous composition as presently disclosed can be used directly in a consumer product without modification. Alternatively, it can be diluted or concentrated accordingly, depending on how it is to be used in preparing a particular consumer product.

Additional examples of consumer products, and formulations thereof, in which an aqueous composition herein can be useful for preparing are disclosed in U.S. Patent. Appl. Publ. Nos. 2015/0257422, 2015/0282513, 2015/0313265 and 2015/0216219, which are all incorporated herein by reference.

Non-limiting examples of compositions and methods disclosed herein include:

1. A method for producing an aqueous composition comprising fructose, the method comprising:
    (a) contacting water, sucrose, and a glucosyltransferase enzyme that synthesizes poly alpha-1,3-glucan having at least 30% alpha-1,3-linkages, to produce a soluble fraction and an insoluble fraction, wherein the insoluble fraction comprises the poly alpha-1,3-glucan, and wherein the soluble fraction comprises at least about 55% fructose on a dry weight basis, and
    (b) separating the soluble fraction from the insoluble fraction, thereby providing an aqueous composition comprising fructose.
2. The method of embodiment 1, wherein the glucosyltransferase enzyme synthesizes poly alpha-1,3-glucan having at least 95% alpha-1,3-linkages.
3. The method of embodiment 1 or 2, wherein the soluble fraction further comprises soluble oligosaccharides with a degree of polymerization (DP) of 2 to about 15.
4. The method of embodiment 3, wherein the soluble fraction comprises less than about 30% of the soluble oligosaccharides on a dry weight basis.
5. The method of embodiment 3 or 4, further comprising contacting the soluble fraction with an alpha-glucosidase enzyme to hydrolyze at least one glycosidic linkage of the oligosaccharides, thereby increasing the monosaccharide content in the soluble fraction (such contacting may be with the soluble fraction of step [a] and/or step [b]).
6. The method of embodiment 1, 2, 3, 4, or 5, wherein the soluble fraction comprises at least about 75% fructose on a dry weight basis.
7. The method of embodiment 1, 2, 3, 4, 5, or 6, wherein the method further comprises a process step that increases the content of monosaccharides relative to the content of other saccharides in the soluble fraction, wherein the process step optionally is nanofiltration or enzymatic hydrolysis.
8. The method of embodiment 1, 2, 3, 4, 5, or 6, wherein the method does not comprise chromatography as a process step to increase the content of fructose relative to the content of other saccharides in the soluble fraction
9. An aqueous composition produced by a method according to embodiment 1, 2, 3, 4, 5, 6, 7, or 8.
10. The aqueous composition of embodiment 9, wherein the aqueous composition is comprised within, or is, an ingestible product, and optionally is used as a sweetener of the ingestible product.
11. An aqueous composition comprising:
    (i) at least about 55% fructose on a dry weight basis,
    (ii) about 3% to about 24% glucose on a dry weight basis, and (iii) soluble oligosaccharides with a degree of polymerization (DP) of 2 to about 15, wherein the oligosaccharides comprise glucose and/or fructose.

12. The aqueous composition of embodiment 11, wherein the soluble oligosaccharides are selected from the group consisting of sucrose, leucrose, trehalulose, isomaltulose, maltulose, isomaltose, and nigerose.

13. The aqueous composition of embodiment 11 or 12, wherein the oligosaccharides comprise (i) at least about 90 wt % glucose, and (ii) about 60-99% alpha-1,3 and about 1-40% alpha-1,6 glucosidic linkages.

14. The aqueous composition of embodiment 11, 12, or 13, wherein the aqueous composition comprises at least about 75% fructose on a dry weight basis.

15. The aqueous composition of embodiment 11, 12, 13, or 14, wherein the aqueous composition comprises less than about 30% of the soluble oligosaccharides on a dry weight basis.

16. The aqueous composition of embodiment 11, 12, 13, 14, or 15, wherein the aqueous composition is comprised within, or is, an ingestible product, and optionally is used as a sweetener of the ingestible product.

17. The aqueous composition of embodiment 16, wherein the aqueous composition has a conductivity less than about 50 μS/cm at about 30 wt % dry solids and an ICUMSA value less than about 50.

18. An ingestible product comprising the aqueous composition of any of claim 11, 12, 13, 14, 15, 16, or 17, wherein the ingestible product is a food, beverage, animal feed, human or animal nutritional product, pharmaceutical product, or oral care product.

EXAMPLES

The present disclosure is further exemplified in Examples 2-6 below. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Abbreviations

The meaning of some of the abbreviations used herein is as follows: "g" means gram(s), "h" means hour(s), "mL" means milliliter(s), "psi" means pound(s) per square inch, "wt %" means weight percentage, "μm" means micrometer(s), "° C." means degrees Celsius, "mg" means milligram(s), "mm" means millimeter(s), "m" means meter(s), "μL" means microliter(s), "mmol" means millimole(s), "min" means minute(s), "mol %" means mole percent, "M" means molar, "mg/g" means milligram per gram, "rpm" means revolutions per minute, "MPa" means megaPascals, "BV" means bed volume, "lbm" means pound-mass, "psis" means pounds per square inch absolute.

General Methods

Analysis of Carbohydrate Composition

An Aminex® HPX-42A column (BioRad, Hercules, Calif.) having deionized water at a flow rate of 0.6 mL/min and a temperature of 85° C. was used to quantitate soluble oligosaccharide byproducts (DP2-DP7). An Aminex® HPX-87C column (BioRad) having deionized water at a flow rate of 0.6 mL/min and a temperature of 85° C. was used to quantitate the level of sucrose, glucose, leucrose and fructose in the soluble reaction products. Use of 2× Aminex® HPX-87C columns in series at the same flow rate and temperature was performed to quantitate the level of all carbohydrates on de-ashed, purified fructose products.

ICUMSA Color Analysis

ICUMSA is a measure of the color of sugar solutions/syrups. This parameter can be measured according to the following protocol using a spectrophotometer. The method used herein for measuring ICUMSA (Table 2) is somewhat iterative, but for very low color materials, it is ideal to measure color using long cells.

TABLE 2

Protocol to Measure ICUMSA of a Syrup

| Step | Description |
|---|---|
| 1 | While agitating with PTFE stir blade, dilute 3.0 g fructose syrup (soluble fraction) with 7.0 g DI water. |
| 2 | Adjust pH to 7.0 using 0.1M NaOH or 0.1M HCl. |
| 3 | Filter solution through 0.45-micron filter. |
| 4 | Measure Brix (g solid/100 g) using a SPER SCIENTIFIC digital refractometer. |
| 5 | Measure density (g/mL) using densitometer. |
| 6 | Calculate concentration c (g solid/mL) as Brix*density/100. |
| 7 | Measure absorbance As at 420 nm using indicated pathlength b in cm. |
| 8 | Calculate ICUMSA as 1000*As/(b*c). |

Conductivity

Conductivity measurements were made using a commercially available conductivity meter (VWR, Radnor, Pa.). Fructose syrups were diluted to 10 wt % dry solids (DS) with deionized water before conductivity measurements were made.

Example 1 (Comparative)

Production of Fructose Syrup Using GTFJ Enzyme

This example discloses the composition of a fructose syrup produced in a poly alpha-1,3-glucan synthesis reaction catalyzed by a GTFJ enzyme (SEQ ID NO:6), and its subsequent composition following leucrose hydrolysis.

GTFJ synthesizes fructose and poly alpha-1,3-glucan coproducts, as well as glucose and oligosaccharide (e.g., DP2-7) byproducts. The poly alpha-1,3-glucan product comprises about 100% alpha-1,3 linkages.

White crystalline sucrose (3000 g) was added to a clean 5-gallon polyethylene bucket. Water (18.1 L) and Fermasure™ (10 mL) were added to the bucket, and the pH was adjusted to 7.0 by addition of 5 vol % NaOH and/or 5 vol % $H_2SO_4$. The final volume was ~20 L and the initial concentration of sucrose as measured by HPLC was 155.3 g/L. A poly alpha-1,3-glucan synthesis reaction was initiated by adding crude gtfJ enzyme (SEQ ID NO:6) extract (prepared as described in the General Methods section) to a concentration of 0.3 vol %. Agitation of the reaction was provided using an overhead mechanical motor equipped with a glass shaft and PTFE blade.

HPLC analysis of the glucan synthesis reaction that had commenced for 65 hours revealed that the sucrose concentration in the soluble fraction was 6.3 g/L; the reaction was deemed to be complete. The soluble fraction of the finished reaction was then filtered away from the insoluble poly alpha-1,3-glucan product, thereby providing a filtrate. The GTF enzyme was deactivated by heating the filtrate to 60° C. for 30 minutes. The filtrate was then treated with TG L-2000 transglucosidase enzyme (1 vol %, DuPont, Wilmington, Del.) at 60° C. for 48 hours under gentle agitation to hydrolyze leucrose. The hydrolyzed filtrate was then concentrated to a total concentration of 870 g/L dry solids using a rotary evaporator, thereby providing a syrup. Table 3 provides the sugar content (dwb) of the filtrate before and after hydrolysis. While hydrolysis of leucrose in the filtrate was successful, the fructose content of the resulting syrup was lower than predicted apparently due to competitive trans-glucosylation and trans-fructosylation reactions occurring during the transglucosidase treatment, whereby the concentration of the oligosaccharides increased (Table 3). The oligosaccharide content comprised primarily DP2-7, though some oligosaccharides up to DP8 or DP9 may have been present.

TABLE 3

Carbohydrate Composition of Filtrates (wt % - Dry Weight Basis)

| Material | Fructose | Glucose | Leucrose | Other DP2 | DP3+ | Total |
|---|---|---|---|---|---|---|
| Filtrate (not hydrolyzed) | 35.1 | 7.5 | 38.6 | 10.0 | 8.8 | 100 |
| Hydrolyzed Filtrate (Actual) | 47.0 | 33.7 | 1.1 | 8.7 | 9.3 | 100 |
| Predicted composition of Hydrolyzed Filtrate | 54.4 | 27.8 | 2.0 | 8.8 | 7.0 | 100 |

The relatively low content of fructose and high content of oligosaccharides in the hydrolyzed filtrate generally renders this syrup unsuitable for use in large-scale applications, such as in the sweetener industry. Furthermore, the final concentration of fructose that was obtained in the glucan synthesis reaction using GTFJ followed by leucrose hydrolysis using TG L-2000 is not higher than the fructose content that can be obtained by inverting sucrose, which can yield a fructose composition of up to 50 wt % (dwb) without further processing.

Thus, alternative methods of using a glucan synthesis reaction to produce fructose syrup were pursued, and are disclosed below.

Example 2

Production of Fructose Syrup Using an Improved GTF Enzyme

This example discloses the composition of a fructose syrup produced in a poly alpha-1,3-glucan synthesis reaction catalyzed by an improved GTF, and its subsequent composition following leucrose hydrolysis.

The amino acid sequence of an *S. salivarius* GTF enzyme that produces poly alpa-1,3-glucan with about 100% alpha-1,3 linkages was modified in its catalytic domain such that the enzyme could produce more products (poly alpha-1,3-glucan and fructose), and less byproducts (e.g., glucose, oligosaccharides such as leucrose), from sucrose substrate, as compared to the enzyme's unmodified counterpart.

Poly alpha-1,3-glucan synthesis reactions using the improved GTF were run in a 5000-gal stainless steel vessel comprising 94 g/L white crystalline sucrose dissolved in water. The pH of the reaction was maintained using 10 mM potassium phosphate as a buffer and adjusted to 5.5 using 2N $H_2SO_4$. An antimicrobial, FermaSure® XL, was added at 100 ppmv to prevent contamination during the reaction. The reactor contained three pitched blade impellers set to 33 rpm and was controlled at 23° C. using cooling water flowing into the jacket of the reactor. The reaction was initiated by adding 30 pounds of the improved GTF enzyme, and deemed complete after 14 hours at which time the sucrose concentration reached less than 2 g/L. At the end of the reaction, the GTF enzyme was deactivated by heating the reaction contents to 65° C. for 30 minutes using an external heat exchanger. This process was repeated in a second reaction ("2.2") comprising a portion of the soluble fraction (490 gallons) produced in the first reaction ("2.1"). The initial contents of reactions 2.1 and 2.2 are summarized in Table 4.

TABLE 4

Polymerization conditions for production of fructose syrup

| Rxn | Water Volume (gal) | Buffer Mass (lbm) | FermaSure® Mass (lbm) | Sucrose Mass (lbm) | Enzyme Mass (lbm) | Soluble Fraction from Rxn 2.1 (gal) |
|---|---|---|---|---|---|---|
| 2.1 | 4751 | 57.4 | 4.2 | 3962 | 30 | N/A |
| 2.2 | 4261 | 57.4 | 4.2 | 3962 | 30 | 490 |

The insoluble poly alpha-1,3-glucan polymer (i.e., insoluble fraction) produced in each reaction was separated from each respective soluble fraction using a filter press, thereby providing a filtrate. Though a filter press was employed to provide a soluble fraction separated from an insoluble fraction, any number of separation processes known in the art could have been used for this purpose. Table 5 provides the sugar content (dwb) of each filtrate.

TABLE 5

Carbohydrate Composition of Reaction 2.1 and 2.2 Filtrates (wt % - Dry Weight Basis)

| Rxn | Fructose | Glucose | Sucrose | Leucrose | Other Oligomers | Total |
|---|---|---|---|---|---|---|
| 2.1 | 70.3 | 7.2 | 2.0 | 13.6 | 6.9 | 100 |
| 2.2 | 64.6 | 7.3 | 2.5 | 17.7 | 7.8 | 100 |

It is apparent from Table 5 that the improved GTF could produce at least about 65-70% fructose on a dry weight basis of the soluble products of the enzyme.

For purposes of leucrose hydrolysis, the remaining filtrate of reaction 2.1 was combined with the filtrate of reaction 2.2 to provide a total of 4740 gal of dilute fructose syrup. The combined dilute syrup (comprising about 67.5 wt % fructose dwb) was treated with sodium thiosulfate for 30 min and adjusted to pH 4.4 and 55° C. TG L-2000 transglucosidase enzyme was added to initiate a hydrolysis reaction, which was agitated for 8.5 hours. Table 6 provides the sugar content (dwb) of the hydrolyzed syrup. Its oligosaccharide content comprised primarily DP2-7, though some oligosaccharides up to DP8 or DP9 may have also been present.

TABLE 6

Carbohydrate Composition of Hydrolyzed Syrup (wt % - Dry Weight Basis)

| Fructose | Glucose | Leucrose | Other DP2[a] | DP3+ | Total |
|---|---|---|---|---|---|
| 70.7 | 15.7 | <1.0 | 10.2 | 3.3 | 100 |

[a]Includes at least sucrose.

Table 6 indicates that, while hydrolysis of leucrose in the filtrate was successful, the fructose content of the resulting syrup was not substantially higher than the pre-hydrolysis fructose level (Table 5). This result may have been due to competitive trans-glucosylation and trans-fructosylation reactions occurring during the transglucosidase treatment, whereby the concentration of non-leucrose oligosaccharides increased.

The hydrolyzed fructose syrup was then concentrated to 70 wt % dry solids (DS) using a plate-and-frame forced circulation evaporator operated with an outlet temperature of 143° F. and a pressure of 1.5-1.6 psia. The concentrated fructose syrup had an ICUMSA color of 2240 and a conductivity of 2200 µS/cm at 10 wt % DS; it was apparent that the evaporation process resulted in color formation in the syrup.

Thus, a syrup comprising at least about 70 wt % fructose on a dry weight basis was prepared. This fructose content (dwb) is sufficiently high for the syrup to be used as a sweetener; however, the amount of oligosaccharides is still quite high. Additionally, the conductivity and color of this material are too high for this syrup to be generally useful in large-scale sweetener applications. Nevertheless, such fructose syrup will lend itself useful to various other downstream applications. Such a feedstock would be suitable for use in fermentation feeds (e.g., to produce ethanol or other fermentation products), animal feeds, or in specialty sweetener applications.

Example 3

Removal of Oligosaccharides from Fructose Syrup by Nanofiltration

This example discloses removing oligosaccharides from the fructose syrup produced in Example 2. This step increased the content of monosaccharides (fructose and glucose) in the syrup relative to other saccharides, and in so doing raised the percent fructose (dwb) of the syrup.

The fructose syrup prepared in Example 2 (sugar content provided in Table 6) was diluted to 41 wt % DS and adjusted to pH 4.45, thereby providing a feed for nanofiltration. The feed was introduced to a nanofiltration system at 65° C. and constantly recirculated until a total fructose yield of 91% was achieved. The unit was equipped with two 4-inch spiral wound modules in parallel. One module contained an OSMONICS DK (General Electric, New York, United States) spiral wound membrane unit containing 6.2 m² surface area, and the other module contained a TS40 (Trisep Corporation, Galeta, Calif.) spiral wound membrane unit containing 7.2 m² surface area. Permeate from the two membranes was combined; the mass balance for the experiment is provided in Table 7. The feed concentration was maintained to the initial concentration by the addition of diafiltration (DF) water. A total of 1.66 kg DF water was added per kg DS in the feed. Two permeate fractions, F1 and F2, were collected. The first fraction, F1, was collected from 0-75% yield and the second fraction, F2, was collected from 75-91% yield, where the yield is defined as kg fructose in the permeate divided by kg fructose in the feed. Both permeates F1 and F2 constituted enriched fructose streams comprising, respectively, 79 and 76 wt % of the dry matter as fructose (Table 7).

TABLE 7

Nanofiltration Mass Balance

| Fraction | wt % DS | kg DS | Fructose Purity (%) |
|---|---|---|---|
| Permeate F1 | 23 | 66 | 79 |
| Permeate F2 | 19 | 11 | 77 |
| Concentrate | 36 | 25 | 26 |
| Feed | 41 | 102 | 68 |

The detailed sugar composition of permeate F1 is provided in Table 8. The concentration (dwb) of fructose in F2 was lower than in F1 due to breakthrough of disaccharides. A preferred membrane herein has low breakthrough of disaccharides at even very high yields of fructose, such as 95% or even 98%. Overall, however, it is apparent from comparing Table 8 with Table 6 that removal of oligosaccharides via nanofiltration is useful for further increasing the content (dwb) of fructose in a syrup. (It should also be apparent that this process would be able to increase the fructose content of a syrup that was not hydrolyzed per Example 2.)

TABLE 8

Carbohydrate Composition of Nanofiltration Permeate F1 (wt % - Dry Weight Basis)

| Fructose | Glucose | DP2$^a$ | DP3+ | Total |
|---|---|---|---|---|
| 79.0 | 19.4 | 1.6 | <0.1 | 100 |

$^a$Includes at least sucrose and leucrose.

The ICUMSA color of permeate F1 was 870, and a corresponding increase in color of the retentate was observed. The conductivity of permeate F1 was 3400 µS/cm, indicating that many of the ions present in the syrup were not rejected during the nanofiltration process.

Thus, a syrup comprising at least about 79 wt % fructose on a dry weight basis was prepared. The use of nanofiltration removed nearly all of the DP3+ oligosaccharides as well as the majority of the DP2 oligosaccharides while simultaneously increasing the fructose content (dwb) in the syrup. While a substantial amount of color was removed from the syrup (compare to ICUMSA >2000 observed in Example 2), its high conductivity and color are generally unsuitable for use in large scale sweetener applications. Again, however, such fructose syrup will lend itself useful to various other downstream applications.

Example 4

Polishing of Fructose Syrup

This example discloses the removal of ions and color by treatment of a fructose syrup with adsorption technology. In particular, the fructose syrups prepared in Examples 2 and 3 were subjected to ion exchange chromatography and activated carbon treatment to decrease the conductivity and ICUMSA of each syrup, while preserving their high fructose content.

Columns containing either strong acid cation (SAC) ion exchange resin (IMAC C16 P), weak base anion (WBA) ion exchange resin (AMBERLITE IRA 92, Dow, Midland, Mich.), or activated carbon (AC) (CHEMVIRON CPG, Calgon Carbon Corporation) were provided accordingly. The columns were configured in series as 1) SAC, 2) WBA, 3) SAC, 4) WBA, and 5) AC. The fructose syrup described in Table 8 was adjusted to a concentration of 52 wt % DS and heated to 60° C. The syrup was then fed to the column series at 2 BV/hr. The conductivity of the syrup over 7 hours of running it through the columns was reduced to between 7.4 and 19 µS/cm, and its ICUMSA color was measured between 1 and 20. The fructose syrup described in Table 6 (adjusted to 10 wt % DS) was polished in a similar manner, yielding a syrup with an ICUMSA color less than 10 and conductivity of 5.5 µS/cm.

Thus, fructose syrup disclosed herein can be polished to remove ample amounts of ions and color therefrom. The low color and low conductivity, coupled with high fructose content, of this syrup render it as being particularly suitable for use in large scale sweetener applications.

Example 5

Characterization of Oligosaccharides in Fructose Syrup

This example describes the DP3+ oligosaccharides present in fructose syrup prepared in a glucan synthesis reaction.

Fructose syrup was produced and concentrated using the methodology described in Example 2, with the exception that treatment with TG L-2000 transglucosidase was omitted. The composition of this syrup is provided in Table 9. The levels of each sugar component are as expected, being in line with the results shown in Table 5 (Example 2).

TABLE 9

Carbohydrate Composition of Fructose Syrup (wt % - Dry Weight Basis)

| Fructose | Glucose | Leucrose | Other DP2$^a$ | DP3+ | Total |
|---|---|---|---|---|---|
| 68.8 | 7.6 | 13.1 | 3.5 | 7.0 | 100 |

$^a$Includes at least sucrose.

Chromatographic separation employing a strong acid cation-exchange resin was used to isolate the oligosaccharide fraction of the syrup. The physical parameters of the column used for this separation appear in Table 10.

TABLE 10

Physical Parameters of the Column Used for Chromatographic Separation

| Resin Type | FINEX CS11GC, #296 |
|---|---|
| Ion form | Na$^+$ |
| Crosslinking, % divinyl benzene | 5.5% |
| Particle size (mm) | 0.35 |
| Bed length (m) | 5.2 |
| Column diameter (m) | 0.225 |

The concentrated syrup was filtered and diluted to 30 g dry solids/100 g solution using ion exchanged tap water. Prior to addition of the diluted syrup to the column resin, the resin was washed with six bed volumes (BV) of sodium chloride solution (three BV at 10 wt % sodium chloride followed by three BV at 5 wt % sodium chloride) to convert the resin to the sodium form. The sugar solution (15 L) was then fed to the column, after which the column was eluted using ion exchanged water at a flow rate of 30 L/h. The run conditions of the chromatographic separation are summarized in Table 11.

TABLE 11

Chromatographic Separation Run Conditions

| Feed size (L) | 15 |
|---|---|
| Feed dry solids (g/100 g) | 30 |
| Column temp (° C.) | 70 |
| Flow rate (L/hr) | 30 |

An oligosaccharide solution eluted between 140 and 185 minutes and was recovered. The oligosaccharide fraction thus prepared was analyzed by HPLC to determine its product distribution. Briefly, the composition of the oligosaccharide fraction was measured using an Agilent 1260 HPLC equipped with a refractive index detector. Separation was realized using a BioRad AMINEX HPX-42A column using water as an eluent at 85° C. and a flow rate of 0.6 mL/min. The composition of the oligosaccharides appears in Table 12.

TABLE 12

Composition of Oligosaccharides Recovered by Fractionation (wt % - Dry Weight Basis)

| DP2 | DP3 | DP4 | DP5 | DP6 | DP7+ |
|---|---|---|---|---|---|
| 11 | 23 | 28 | 21 | 12 | 5 |

The oligosaccharide fraction described in Table 12 was subjected to partially methylated alditol acetate (PMAA) analysis (following methodology in Pettolino et al., Nature Protocols 7:1590-1607) and analyzed by GC-MS. Briefly, the sample was treated with DMSO anion and iodomethane to methylate hydroxyl groups, and then hydrolyzed with trifluoroacetic acid. The hydroxyl groups resulting from the broken glycosidic linkages were then acetylated with acetic anhydride, and the resulting glucitols were analyzed by GC/MS. The oligosaccharides were found to have the distribution described in Table 13 (all linkages therein believed to be alpha). The dominant linkage was alpha-1,3. No terminal fructose was detected in this oliaosaccharide fraction.

TABLE 13

Linkage Distribution of Oligosaccharides

| Linkage | Linkage % |
|---|---|
| 1→3 | 87.5 |
| 1→6 | 7.3 |
| 1→3, 6 | 2.8 |
| 1→4 | 1.0 |
| 1→2, 3 | 0.7 |
| 1→2 | 0.6 |
| 1→3, 4 | 0.3 |

Thus, DP3+ oligosaccharides present in fructose syrup prepared in a glucan synthesis reaction herein were characterized.

Example 6

Characterization of Disaccharides Present in Fructose Syrup

This example discloses the nature of the disaccharides present in fructose syrups prepared herein. It was found that fructose syrup can comprise at least the disaccharides sucrose, maltulose, leucrose, trehalulose, isomaltulose, and isomaltose. While not directly detected in the present composition, the high level of alpha 1→3 linkages in the oligosaccharides suggests that nigerose could be present in aqueous compositions produced using the techniques described in the present disclosure.

The purified fructose syrups described in Tables 6 (hydrolyzed syrup) and 8 (hydrolyzed and nanofiltrated syrup) were characterized extensively to identify the oligosaccharides present therein. Specifically, disaccharides were identified in syrup by two different methods: GC-MS and HPAEC-PAD-MS (High Performance Anion Exchange Chromatography-Pulsed Amperometric Detection and Mass Spectrometric detection).

The materials were derivatized by oximation and silylation before being analyzed by GC-MS (*J. Agric. Food Chem.*, 19:551-554). Briefly, each syrup was dried down and the material of each was treated with hydroxylamine hydrochloride in pyridine, and then with hexamethyldisilazane and trifluoroacetic acid to complete the reaction. Separation was done on a 14% cyanopropyl-phenyl 86% dimethyl polysiloxane column with a mass-selective detector operating in full scan mode. FIG. 1 shows a distribution of certain disaccharides (sucrose, maltulose, leucrose, turanose, trehalulose, isomaltulose, isomaltose) present in the fructose syrup of Table 6, as detected by GC-MS.

Figure 2:
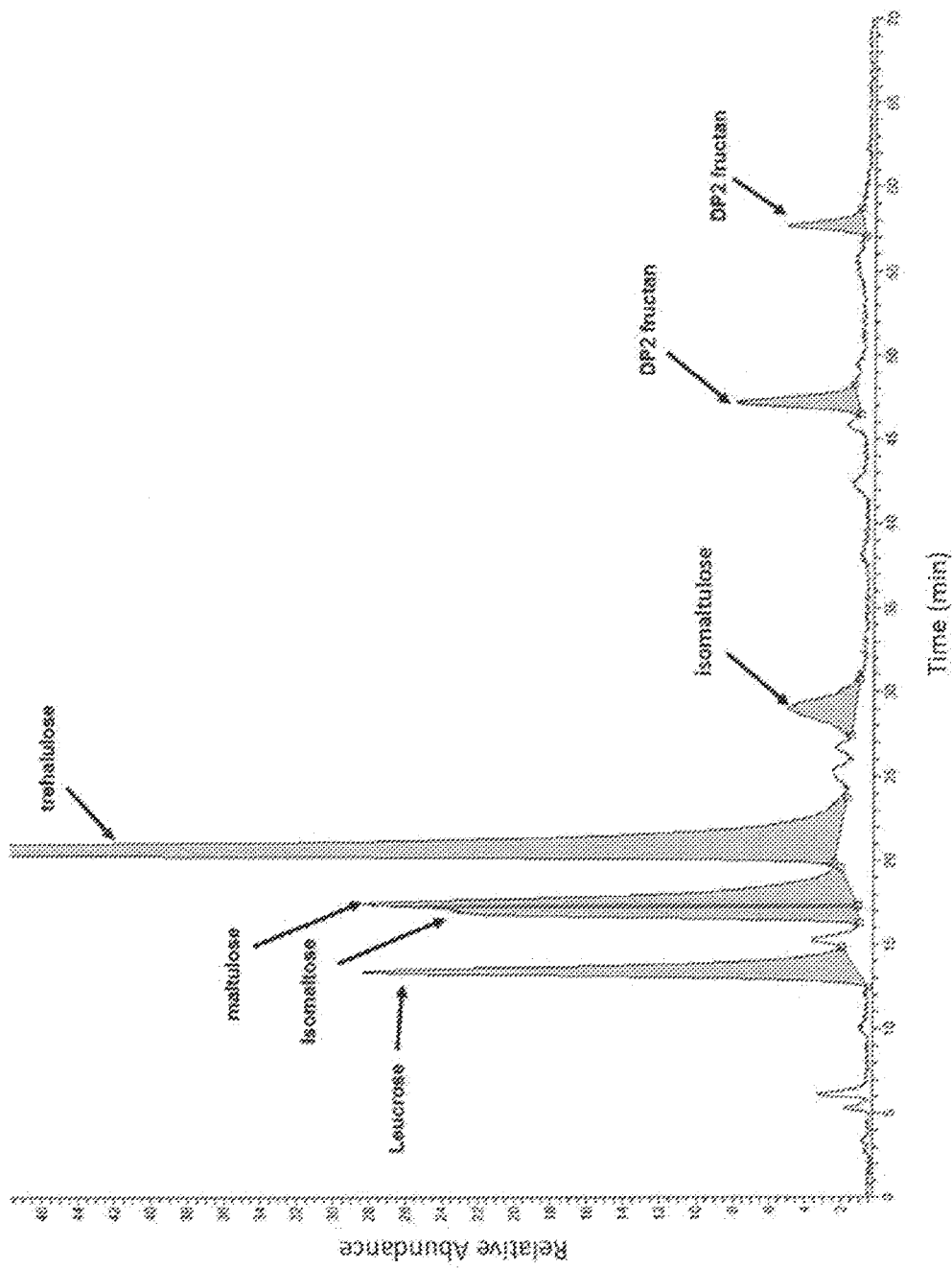
FIG. 2 shows a distribution of disaccharides present in the hydrolyzed fructose syrup of Table 6, as detected by HPAEC-PAD-MS.

Disaccharides were also identified by HPAEC-PAD-MS using a PA20 column with sodium hydroxide gradient, or LC-MS with separation on two in-series HPX-87C columns. Disaccharides such as sucrose, maltulose, leucrose, trehalulose, isomaltulose, and isomaltose were identified in the fructose syrup of Table 6 by matching the retention time and mass spectra (product ion spectra for HPAEC-PAD-MS and electron ionization [EI] spectra for GC-MS) of a disaccharide authentic standard with those of the disaccharide peaks detected in the material separated on the PA20 column (FIG. 2). Some disaccharide peaks could not be matched to any of the commercially available disaccharide standards composed of glucose or glucose and fructose. These unmatched peaks were postulated to be fructan disaccharides that are present, for example, in honey. Although the exact structure and linkage of these DP2 fructans were not established, the disaccharide fructans present in the fructose syrup were identical to those observed in alfalfa honey (data not shown) and a commercial sample of ISOCLEAR 42 HFCS obtained from Cargill (Wayzata, Minn.) (data not shown). The identity of the fructans present in the fructose syrup was established by comparing the product ion spectra and retention times of fructan disaccharides versus those of the alfalfa honey or ISOCLEAR 42 HFCS samples.

Thus, the disaccharide content of fructose syrup prepared in a glucan synthesis reaction herein was characterized.

What is claimed is:

1. A method for producing fructose, said method comprising:
   contacting water, sucrose, and a glucosyltransferase enzyme that synthesizes poly alpha-1,3-glucan having at least 30% alpha-1,3-linkages to produce a soluble fraction and an insoluble fraction,
   wherein the insoluble fraction comprises said poly alpha-1,3-glucan,
   wherein the soluble fraction comprises at least 55% fructose on a dry weight basis, and
   wherein the method does not comprise a process step that increases the content of fructose relative to the content of other saccharides in the soluble fraction.

2. The method of claim 1, wherein the glucosyltransferase enzyme synthesizes poly alpha-1,3-glucan having at least 95% alpha-1,3-linkages.

3. The method of claim 1, wherein the soluble fraction further comprises soluble oligosaccharides with a degree of polymerization (DP) of 2 to about 15.

4. The method of claim 3, wherein the soluble fraction comprises less than about 30% of said soluble oligosaccharides on a dry weight basis.

5. The method of claim 1, wherein the soluble fraction comprises at least about 75% fructose on a dry weight basis.

6. The method of claim 1, wherein the sucrose concentration of the soluble fraction is less than 2 g/L.

7. The method of claim 1, further comprising separating the soluble fraction from the insoluble fraction.

* * * * *